United States Patent [19]

Kawagishi et al.

[11] Patent Number: 5,605,788
[45] Date of Patent: Feb. 25, 1997

[54] SILVER HALIDE COLOR PHOTOGRAPHIC MATERIAL

[75] Inventors: Toshio Kawagishi; Takeshi Nakamine; Masuji Motoki, all of Kanagawa, Japan

[73] Assignee: Fuji Photo Film Co., Ltd., Minami-Ashigara, Japan

[21] Appl. No.: 556,141

[22] Filed: Nov. 9, 1995

[30] Foreign Application Priority Data

Nov. 14, 1994 [JP] Japan ................... 6-279295

[51] Int. Cl.$^6$ .................................. G03C 7/38
[52] U.S. Cl. .......................... 430/558; 430/387
[58] Field of Search .................. 430/558, 386, 430/387

[56] References Cited

U.S. PATENT DOCUMENTS

| | | |
|---|---|---|
| 4,835,094 | 5/1989 | Wolff et al. . |
| 4,845,022 | 7/1989 | Wolff .................. 430/558 |
| 4,916,051 | 4/1990 | Tachibana et al. ........ 430/558 |
| 5,234,805 | 8/1993 | Tang et al. . |
| 5,302,496 | 4/1994 | Romanet et al. ......... 430/387 |
| 5,302,502 | 4/1994 | Shibata ................ 430/558 |

FOREIGN PATENT DOCUMENTS

| | | |
|---|---|---|
| 0443530 | 8/1991 | European Pat. Off. . |
| 3040144 | 2/1988 | Japan .................. 430/558 |
| 323537 | 12/1993 | Japan .................. 430/558 |

*Primary Examiner*—Lee C. Wright
*Attorney, Agent, or Firm*—Birch, Stewart, Kolasch & Birch, LLP

[57] ABSTRACT

A silver halide color photographic material containing a pyrazolotriazole coupler represented by the following formula (I) or (II):

wherein $R_1$ represents a hydrogen atom, a halogen atom, or a substituent; X represents a hydrogen atom, a halogen atom, or a group capable of being splitted off by the reaction with an oxidation product of a developing agent; $L_1$ represents an (n+1)-valent linking group; $L_2$ represents a group represented by the following formula (III); and n represents 1 or 2, and when n is 2, two $L_2$'s may be the same or different;

$$-[(A_1)_a(B_1)_b(A_2)_c(B_2)_d(A_3)_e(B_3)_f(A_4)_g(B_4)_h] \quad (III)$$

wherein $A_1$, $A_2$, $A_3$ and $A_4$ each represents —O—, —S—, —NR$_2$—, —N(R$_2$)CO—, —CON(R$_2$)—, —N(R$_2$)SO$_2$—, —SO$_2$N(R$_2$)—, —CO$_2$—, —OCO—, —N(R$_2$)CON(R$_3$)—, —OCON(R$_2$)— or —N(R$_2$)CO$_2$—; $R_2$ and $R_3$ each represents a hydrogen atom, an alkyl group, an aryl group, an acyl group, an alkanesulfonyl group or an arenesulfonyl group; $B_1$, $B_2$ and $B_3$ each represents an alkylene group or an arylene group; $B_4$ represents an alkyl group or an aryl group; a, b, c, d, e, f and g each represents 0 or 1, and h represents 1, provided that a-b=0, c-d=0 and e-f=0; and at least one group represented by $R_2$, $R_3$, $B_1$, $B_2$, $B_3$ and $B_4$ in the substituents represented by $L_2$ has a group represented by the following formula (IV):

$$-A-NH-R_4 \quad (IV)$$

wherein A represents —CO— or —SO$_2$—; and $R_4$ represents a hydrogen atom or an alkyl group.

10 Claims, No Drawings

SILVER HALIDE COLOR PHOTOGRAPHIC MATERIAL

FIELD OF THE INVENTION

The present invention relates to a silver halide color photographic material and, in particular, relates to a silver halide color photographic material which contains a pyrazolotriazole based magenta coupler, and is improved in color reproducibility, color forming property, and light fastness of a magenta dye.

BACKGROUND OF THE INVENTION

A silver halide color photographic material, in general, contains couplers which form yellow, magenta and cyan dyes upon coupling reaction with the oxidation product of an aromatic primary amine developing agent. As magenta couplers, 1H-pyrazolo[1,5-b][1,2,4]triazole disclosed in U.S. Pat. No. 4,540,654 and 1H-pyrazolo[3,2-c][1,2,4]triazole disclosed in U.S. Pat. No. 3,725,067 are known as preferred couplers because of forming magenta dyes having less unnecessary absorption. However, when the specific compounds of the pyrazolotriazole magenta couplers disclosed in the patents are incorporated into a silver halide color photographic material, there are problems in that the color forming property and the storage stability of the color images are not sufficient. For solving these problems, the substituents of the pyrazolotriazole couplers at the 2-position or 3-position, and the 6-position have been variously contrived. In particular, the 1H-pyrazolo[1,5-b][1,2,4]triazole couplers disclosed in JP-B-3-80296 (the term "JP-B" as used herein refers to an "examined Japanese patent publication"), JP-A-61-65248 (the term "JP-A" as used herein refers to a "published unexamined Japanese patent application"), JP-B-4-3860, JP-B-5-39293, JP-B-5-40892, JP-A-6-222529 and JP-A-6-222532 have been improved in the color forming property but it cannot be said to be sufficient yet. Further, in color reversal films and color negative films, it is preferred to make the thickness of the light-sensitive layer as thin as possible for the improvement of sharpness. Therefore, the development of couplers which have sufficient color forming property even when dispersed with a small amount of high boiling point organic solvents has been desired.

SUMMARY OF THE INVENTION

An object of the present invention is to provide a silver halide color photographic material which has high color forming property.

Another object of the present invention is to provide a silver halide color photographic material which has high light fastness of color images.

These and other objects of the present invention have been attained by a silver halide color photographic material containing a pyrazolotriazole coupler represented by the following formula (I) or (II):

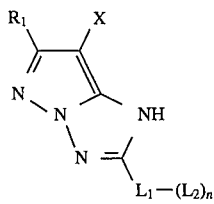
(I)

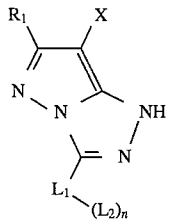
(II)

wherein $R_1$ represents a hydrogen atom, a halogen atom, or a substituent; X represents a hydrogen atom, a halogen atom, or a group capable of being splitted off by the reaction with an oxidation product of a developing agent; $L_1$ represents an (n+1)-valent linking group; $L_2$ represents a group represented by the following formula (III); and n represents 1 or 2, and when n is 2, two $L_2$'s may be the same or different;

$$—[(A_1)_a(B_1)_b(A_2)_c(B_2)_d(A_3)_e(B_3)_f(A_4)_g(B_4)_h]$$ (III)

wherein $A_1$, $A_2$, $A_3$ and $A_4$ each represents —O—, —S—, —$NR_2$—, —$N(R_2)$CO—, —CON($R_2$)—, —N($R_2$)$SO_2$—, —$SO_2$N($R_2$)—, —$CO_2$—, —OCO—, —N($R_2$)CON($R_3$)—, —OCON($R_2$)— or —N($R_2$)$CO_2$—; $R_2$ and $R_3$ each represents a hydrogen atom, an alkyl group, an aryl group, an acyl group, an alkanesulfonyl group or an arenesulfonyl group; $B_1$, $B_2$ and $B_3$ each represents an alkylene group or an arylene group; $B_4$ represents an alkyl group or an aryl group; a, b, c, d, e, f and g each represents 0 or 1, and h represents 1, provided that a-b=0, c-d=0 and e-f=0; and at least one group represented by $R_2$, $R_3$, $B_1$, $B_2$, $B_3$ and $B_4$ in the substituents represented by $L_2$ has a group represented by the following formula (IV):

$$—A—NH—R_4$$ (IV)

wherein A represents —CO— or —$SO_2$—; and $R_4$ represents a hydrogen atom or an alkyl group.

DETAILED DESCRIPTION OF THE INVENTION

The couplers of the present invention are described in detail below.

In formulae (I) and (II), $R_1$ represents a hydrogen atom, a halogen atom (e.g., fluorine, chlorine, bromine), an alkyl group (a straight chain or branched chain alkyl group preferably having from 1 to 32 carbon atoms, e.g., methyl, ethyl, propyl, isopropyl, butyl, t-butyl, 1-octyl, tridecyl), a cycloalkyl group (a cycloalkyl group preferably having from 3 to 8 carbon atoms, e.g., cyclopropyl, cyclopentyl, cyclohexyl, 1-norbornyl, 1-adamantyl), an alkenyl group (an alkenyl group preferably having from 2 to 32 carbon atoms, e.g., vinyl, allyl, 3-buten-1-yl), an aryl group (an aryl group preferably having from 6 to 32 carbon atoms, e.g., phenyl, 1-naphthyl, 2-naphthyl), a heterocyclic group (a 5- to 8-membered heterocyclic group preferably having from 1 to 32 carbon atoms, e.g., 2-thienyl, 4-pyridyl, 2-furyl, 2-pyrimidinyl, 1-pyridyl, 2-benzothiazolyl, 1-imidazolyl, 1-pyrazolyl, benzotriazol-2-yl), a cyano group, a silyl group (a silyl group preferably having from 3 to 32 carbon atoms, e.g., trimethylsilyl, triethylsilyl, tributylsilyl, t-butyldimethylsilyl, t-hexyldimethylsilyl), a hydroxy group, a nitro group, an alkoxy group (an alkoxy group preferably having from 1 to 32 carbon atoms, e.g., methoxy, ethoxy, 1-butoxy, 2-butoxy, isopropoxy, t-butoxy, dodecyloxy), a cycloalkyloxy group (a cycloalkyloxy group preferably having from 3 to 8 carbon atoms, e.g., cyclopentyloxy, cyclohexyloxy), an aryloxy group (an aryloxy group preferably having from 6 to 32 carbon atoms, e.g., phenoxy, 2-naphthoxy), a heterocyclic oxy group (a heterocyclic oxy group preferably having from 1 to 32 carbon atoms, e.g., 1-phenyltetrazol-5-oxy, 2-tetrahydropiranyloxy, 2-furyloxy), a silyloxy group (a silyloxy group preferably having from 1 to 32 carbon atoms, e.g., trimethylsilyloxy, t-butyldimethylsilyloxy, diphenylmethylsilyloxy), an acyloxy group (an acyloxy group preferably having from 2 to 32 carbon atoms, e.g., acetoxy, pivaloyloxy, benzoyloxy, dodecanoyloxy), an alkoxycarbonyloxy group (an alkoxycarbonyloxy group preferably having from 2 to 32 carbon atoms, e.g., ethoxycarbonyloxy, t-butoxycarbonyloxy), a cycloalkyloxycarbonyloxy group (a cycloalkyloxycarbonyloxy group preferably having from 4 to 9 carbon atoms, e.g., cyclohexyloxycarbonyloxy), an aryloxycarbonyloxy group (an aryloxycarbonyloxy group preferably having from 7 to 32 carbon atoms, e.g., phenoxycarbonyloxy), a carbamoyloxy group (a carbamoyloxy group preferably having from 1 to 32 carbon atoms, e.g., N,N-dimethylcarbamoyloxy, N-butylcarbamoyloxy), a sulfamoyloxy group (a sulfamoyloxy group preferably having from 1 to 32 carbon atoms, e.g., N,N-diethylsulfamoyloxy, N-propylsulfamoyloxy), an alkanesulfonyloxy group (an alkanesulfonyloxy group preferably having from 1 to 32 carbon atoms, e.g., methanesulfonyloxy, hexadecanesulfonyloxy), an arenesulfonyloxy group (an arenesulfonyloxy group preferably having from 6 to 32 carbon atoms, e.g., benzenesulfonyloxy), an acyl group (an acyl group preferably having from 1 to 32 carbon atoms, e.g., formyl, acetyl, pivaloyl, benzoyl, tetradecanoyl), an alkoxycarbonyl group (an alkoxycarbonyl group preferably having from 2 to 32 carbon atoms, e.g., methoxycarbonyl, ethoxycarbonyl, octadecyloxycarbonyl), a cycloalkyloxycarbonyl group (a cycloalkyloxycarbonyl group preferably having from 2 to 32 carbon atoms, e.g., cyclohexyloxycarbonyl), an aryloxycarbonyl group (an aryloxycarbonyl group preferably having from 7 to 32 carbon atoms, e.g., phenoxycarbonyl), a carbamoyl group (a carbamoyl group preferably having from 1 to 32 carbon atoms, e.g., carbamoyl, N,N-dibutylcarbamoyl, N-ethyl-N-octylcarbamoyl, N-propylcarbamoyl), an amino group (an amino group preferably having 32 or less carbon atoms, e.g., amino, methylamino, N,N-dioctylamino, tetradecylamino, octadecylamino), an anilino group (an anilino group preferably having from 6 to 32 carbon atoms, e.g., anilino, N-methylanilino), a heterocyclic amino group (a heterocyclic amino group preferably having from 1 to 32 carbon atoms, e.g., 4-pyridylamino), a carbonamido group (a carbonamido group preferably having from 2 to 32 carbon atoms, e.g., acetamido, benzamido, tetradecanamido), a ureido group (a ureido group preferably having from 1 to 32 carbon atoms, e.g., ureido, N,N-dimethylureido, N-phenylureido), an imido group (an imido group preferably having 10 or less carbon atoms, e.g., N-succinimido, N-phthalimido), an alkoxycarbonylamino group (an alkoxycarbonylamino group preferably having from 2 to 32 carbon atoms, e.g., methoxycarbonylamino, ethoxycarbonylamino, t-butoxycarbonylamino, octadecyloxycarbonylamino), an aryloxycarbonylamino group (an aryloxycarbonylamino group preferably having from 7 to 32 carbon atoms, e.g., phenoxycarbonylamino), a sulfonamido group (a sulfonamido group preferably having from 1 to 32 carbon atoms, e.g., methanesulfonamido, butanesulfonamido, benzenesulfonamido, hexadecanesulfonamido), a sulfamoylamino group (a sulfamoylamino group preferably having from 1 to 32 carbon atoms, e.g., N,N-dipropylsulfamoylamino, N-ethyl-N-dodecylsulfamoylamino), an azo group (an azo group preferably having from 1 to 32 carbon atoms, e.g., phenylazo), an alkylthio group (an alkylthio group preferably having from 1 to 32 carbon atoms, e.g., ethylthio, octylthio), an arylthio group (an arylthio group preferably having from 6 to 32 carbon atoms, e.g., phenylthio), a heterocyclic thio group (a heterocyclic thio group preferably having from 1 to 32 carbon atoms, e.g., 2-benzothiazolylthio, 2-pyridylthio, 1-phenyltetrazolylthio), an alkylsulfinyl group (an alkylsulfinyl group preferably having from 1 to 32 carbon atoms, e.g., dodecanesulfinyl), an arenesulfinyl group (an arenesulfinyl group preferably having from 6 to 32 carbon atoms, e.g., benzenesulfinyl), an alkanesulfonyl group (an alkanesulfonyl group preferably having from 1 to 32 carbon atoms, e.g., methanesulfonyl, octanesulfonyl), an arenesulfonyl group (an arenesulfonyl group preferably having from 6 to 32 carbon atoms, e.g., benzenesulfonyl, 1-naphthalenesulfonyl), a sulfamoyl group (a sulfamoyl group preferably having 32 or less carbon atoms, e.g., sulfamoyl, N,N-dipropylsulfamoyl, N-ethyl-N-dodecylsulfamoyl), a sulfo group, or a phosphinoyl group (a phosphinoyl group preferably having from 1 to 32 carbon atoms, e.g., phenoxyphosphinoyl, octyloxyphosphinoyl, phenylphosphinoyl).

The groups represented by $R_1$ may further have a substituent, and examples of preferred substituents include a halogen atom, an alkyl group, a cycloalkyl group, an alkenyl group, an aryl group, a heterocyclic group, a cyano group, a silyl group, a hydroxyl group, a carboxyl group, a nitro group, an alkoxy group, an aryloxy group, a heterocyclic oxy group, a silyloxy group, an acyloxy group, an alkoxycarbonyloxy group, a cycloalkyloxycarbonyloxY group, an aryloxycarbonyloxy group, a carbamoyloxy group, a sulfamoyloxy group, an alkanesulfonyloxy group, an arenesulfonyloxy group, an acyl group, an alkoxycarbonyl group, a cycloalkyloxycarbonyl group, an aryloxycarbonyl group, a carbamoyl group, an amino group, an anilino group, a heterocyclic amino group, a carbonamido group, an alkoxycarbonylamino group, an aryloxycarbonylamino group, a ureido group, a sulfonamido group, a sulfamoylamino group, an imido group, an alkylthio group, an arylthio group, a heterocyclic thio group, a sulfinyl group, a sulfo group, an alkanesulfonyl group, an arenesulfonyl group, a sulfamoyl group and a phosphinoyl group, and preferred carbon atom numbers and specific examples of these groups are the same as those described in the groups represented by $R_1$.

In formulae (I) and (II), X represents a hydrogen atom, a halogen atom or a group capable of being splitted off by the reaction with an oxidation product of a developing agent. Specifically, the group capable of being splitted off includes an alkoxy group, an aryloxy group, an acyloxy group, a carbamoyloxy group, a sulfonyloxy group, a carbonamido group, a sulfonamido group, a carbamoylamino group, a heterocyclic group, an arylazo group, an alkylthio group, an arylthio group, a heterocyclic thio group, etc. The preferred range and specific examples of the halogen atom and the group capable of being splitted off are the same as those described in the groups represented by $R_1$. In some case, X may be a bis type coupler of 4-equivalent couplers of two molecules connected via aldehyde or ketone. Further, X may be a photographically useful group such as a development accelerator, a development inhibitor, a desilvering accelerator or a leuco dye or precursors thereof.

In formulae (I) and (II), $L_1$ represents an (n+1)-valent linking group. In detail, $L_1$ represents an (n+1)-valent linking group having bonds removing (n+1)•hydrogen atoms from alkane, alkene or alkine having from 1 to 20 carbon atoms or from arene having from 6 to 20 carbon atoms.

In formulae (I) and (II), $L_2$ represents a group represented by the following formula (III).

—[(A$_1$)$_a$(B$_1$)$_b$(A$_2$)$_c$(B$_2$)$_d$(A$_3$)$_e$(B$_3$)$_f$(A$_4$)$_g$(B$_4$)$_h$]   (III)

wherein A$_1$, A$_2$, A$_3$ and A$_4$ each represents —O—, —S—, -NR$_2$-, —N(R$_2$)CO—, —CON(R$_2$)—, —N(R$_2$)SO$_2$—, —SO$_2$N(R$_2$)—, —CO$_2$—, —OCO—, —N(R$_2$)CON(R$_3$)—, —OCON(R$_2$)— or —N(R$_2$)CO$_2$—. R$_2$ and R$_3$ each represents a hydrogen atom, an alkyl group, an aryl group, an acyl group, an alkanesulfonyl group or an arenesulfonyl group, and preferred carbon atom numbers and specific examples of these groups are the same as those described in the alkyl group, aryl group, acyl group, alkanesulfonyl group or arylsulfonyl group represented by R$_1$. B$_1$, B$_2$ and B$_3$ each represents an alkylene group (an alkylene group the principal chain of which has preferably from 1 to 10 carbon atoms and the total carbon atom number including the substituents is from 1 to 30, e.g., methylene, ethylene, propylene, butylene) or an arylene group (an arylene group having from 6 to 30 carbon atoms, e.g., 1,2-phenylene, 1,3-phenylene, 1,4-phenylene, 1,2-naphthylene, 1,4-naphthylene). B$_4$ represents an alkyl group or an aryl group, and preferred carbon atom numbers and specific examples of these alkyl and aryl groups are the same as those described in the groups represented by R$_1$. The groups represented by R$_2$, R$_3$, B$_1$, B$_2$, B$_3$ and B$_4$ may further have substituents and preferred substituents are the same as those enumerated as preferred substituents for the groups represented by R$_1$.

a, b, c, d, e, f and g each represents 0 or 1, and h represents 1, provided that a-b=0, c-d=0 and e-f=0.

At least one group represented by R$_2$, R$_3$, B$_1$, B$_2$, B$_3$ and B$_4$ in the substituents represented by L$_2$ has a group represented by the following formula (IV):

—A—NH—R$_4$   (IV)

wherein A represents —CO— or —SO$_2$—. R$_4$ represents a hydrogen atom or an alkyl group, and preferred carbon atom numbers and specific examples of the alkyl group are the same as those described in the alkyl group represented by R$_1$. The groups represented by R$_4$ may further have substituents and preferred substituents are the same as those enumerated as preferred substituents for the groups represented by R$_1$.

The groups represented by R$_2$, R$_3$, B$_1$, B$_2$, B$_3$ and B$_4$ may have a hydroxyl group or an alkyl group having a hydroxyl group as a substituent.

Preferred examples of the compounds of the present invention are described below.

In formulae (I) and (II), R$_1$ preferably represents an alkyl group, an aryl group, an alkoxy group, an aryloxy group, an alkylthio group, an arylthio group, a ureido group, an alkoxycarbonylamino group, an aryloxycarbonylamino group or an amido group. Specific examples of the preferred groups represented by R$_1$ are shown below.

CH$_3$—, C$_2$H$_5$—, (CH$_3$)$_2$CH—, (CH$_3$)$_3$C—,

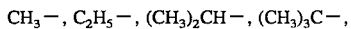

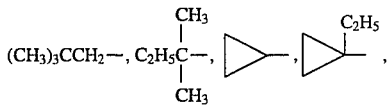

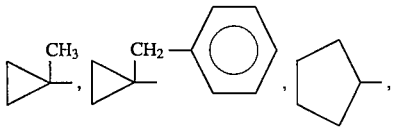

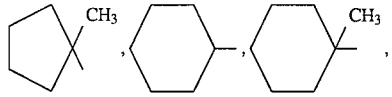

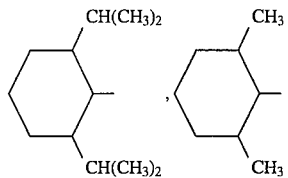

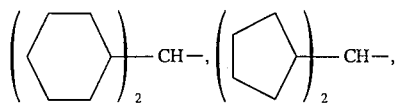

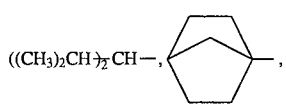

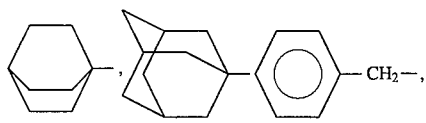

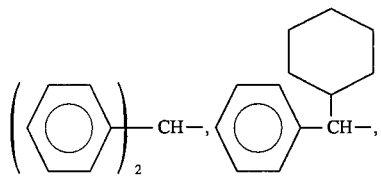

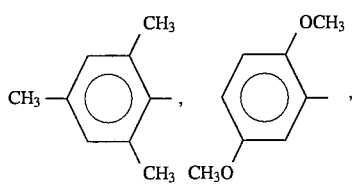

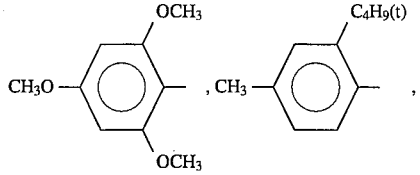

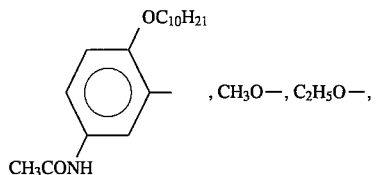

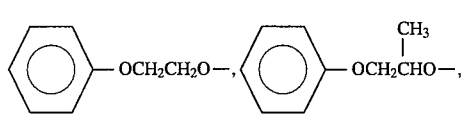

, CH$_3$O—, C$_2$H$_5$O—,

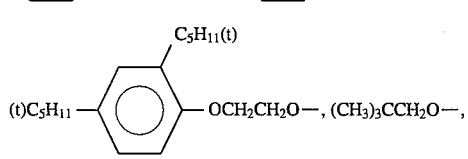

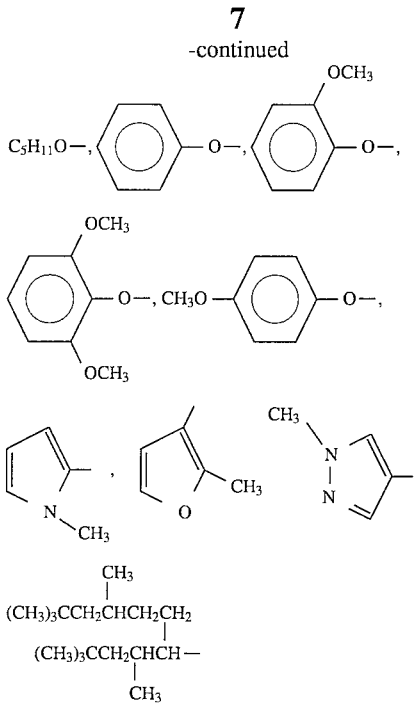

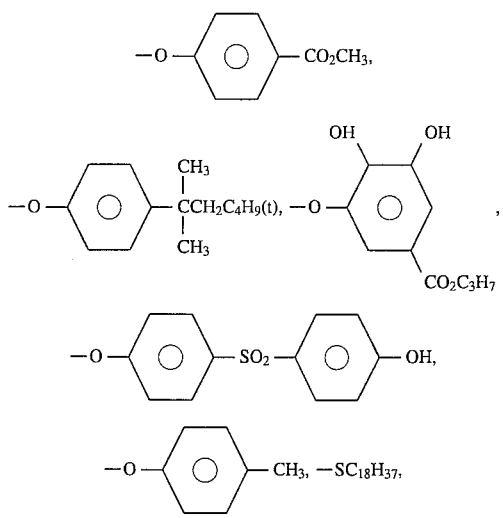

Of these compounds, a primary or secondary alkyl group, an alkoxy group and an aryloxy group are preferred for high color forming property, and a tertiary alkyl group or an aryloxy group are preferred for light and heat fastness of a color image. As the group represented by $R_1$, an alkyl group is more preferred and a tertiary alkyl group is still more preferred.

In formulae (I) and (II), X preferably represents a halogen atom, an aryloxy group, a carbamoyloxy group, an acyloxy group, a heterocyclic group, an arylazo group, an alkylthio group, an arylthio group or a heterocyclic thio group, more preferably a halogen atom, an aryloxy group, a heterocyclic group, an alkylthio group, an arylthio group or a heterocyclic thio group, and most preferably a chlorine atom or an aryloxy group. Specific examples of the preferred groups represented by X are shown below.

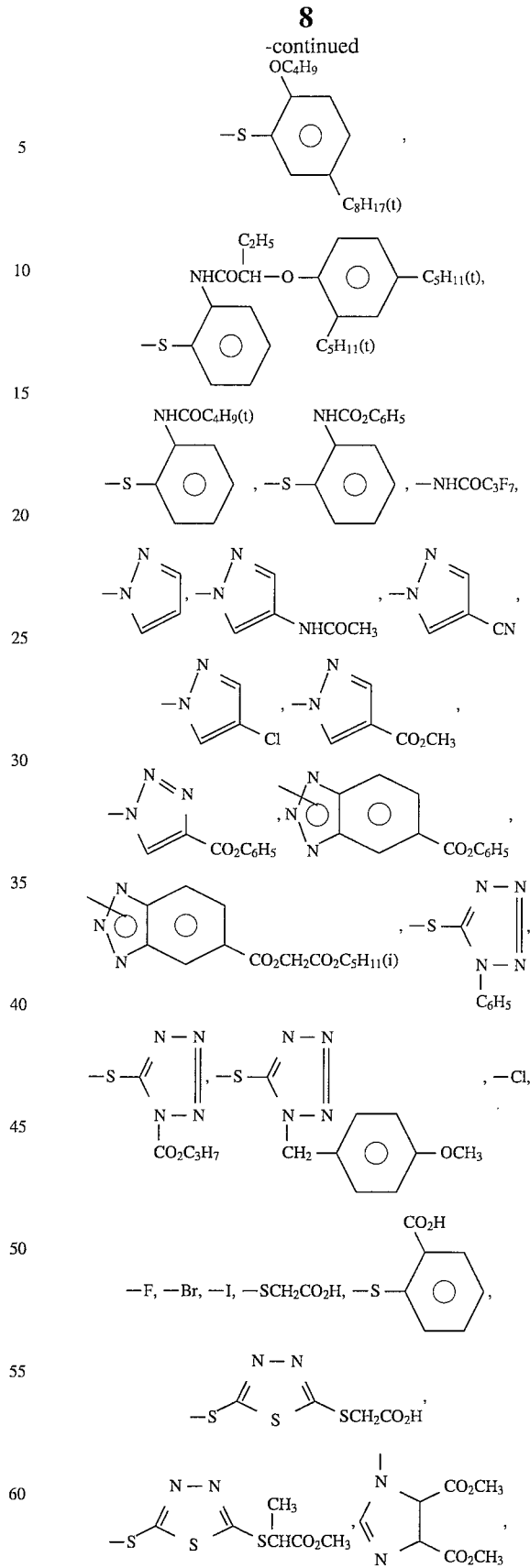

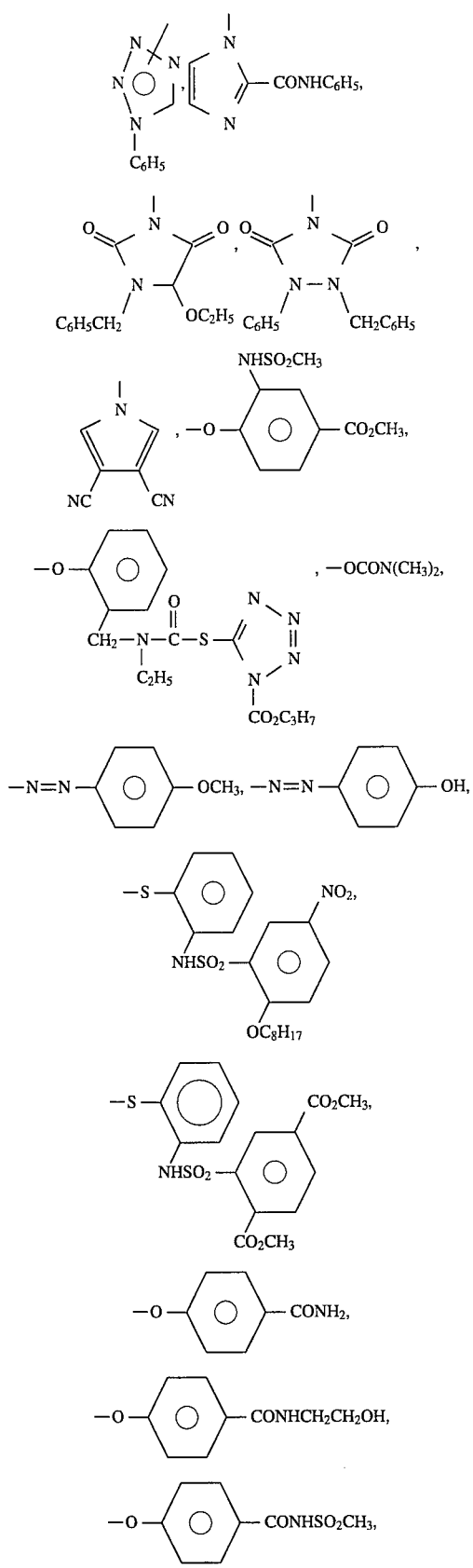

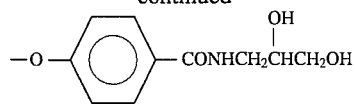

In formulae (I) and (II), $L_1$ preferably represents a substituted or unsubstituted alkylene group the principal chain of which has preferably from 1 to 3 carbon atoms, a substituted or unsubstituted 1,2-phenylene group, a substituted or unsubstituted 1,3-phenylene group or a substituted or unsubstituted 1,4-phenylene group. Specific examples of preferred groups represented by $L_1$ are shown below. The mark * represents the position at which it is connected to a pyrazolotriazole nucleus.

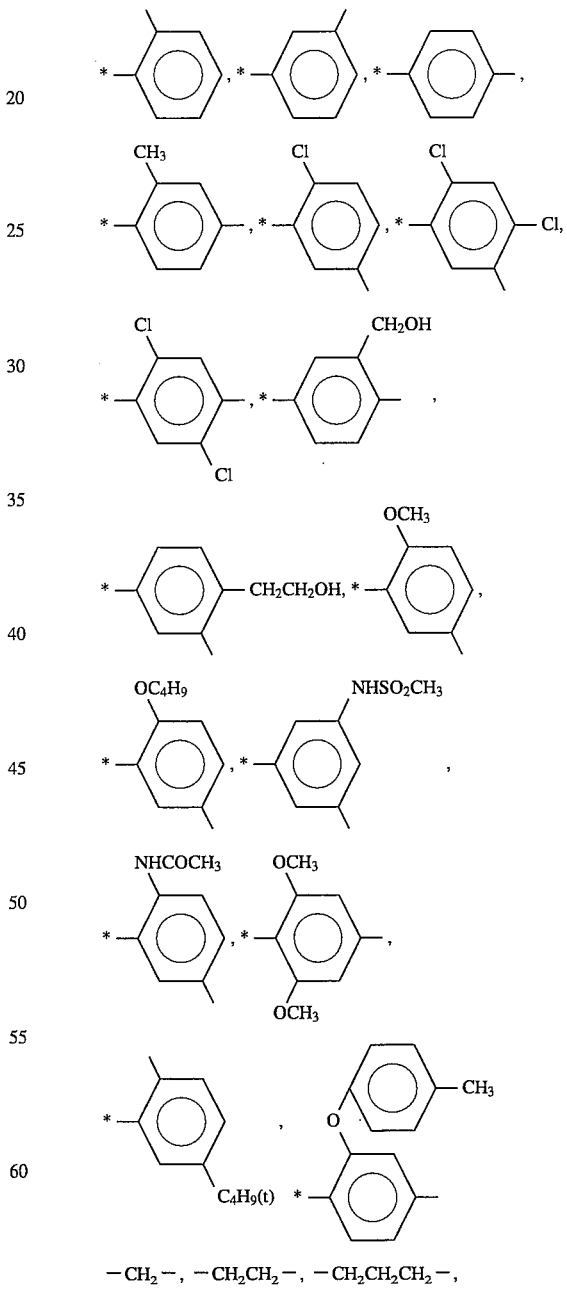

-continued $$-\overset{CH_3}{\underset{|}{CH}}-, -\overset{CH_3}{\underset{\underset{CH_3}{|}}{\overset{|}{C}}}-, -\overset{C_6H_{13}}{\underset{|}{CH}}-, -\overset{C_{10}H_{21}}{\underset{|}{CH}}-,$$

$$-\overset{C_{12}H_{25}}{\underset{|}{CH}}-, -\overset{CH_2OH}{\underset{|}{CH}}-, *-CH_2\overset{}{\underset{\underset{OH}{|}}{CH}}-,$$

$$-\overset{CH_3}{\underset{\underset{CH_2OH}{|}}{\overset{|}{C}}}-, -\overset{CH_2OH}{\underset{\underset{CH_2OH}{|}}{\overset{|}{C}}}-, -CH_2-\overset{}{\underset{\underset{OH}{|}}{CH}}-CH_2-,$$

$$-\overset{CH_3}{\underset{\underset{CH_2CH_2OH}{|}}{\overset{|}{C}}}-, *-CH_2-CH_2-\overset{}{\underset{\underset{CH_3}{|}}{CH}}-, *-\overset{}{\underset{\underset{CH_3}{|}}{CHCH_2}}-,$$

$$*-\overset{CH_3}{\underset{\underset{CH_3}{|}}{\overset{|}{C}}}-CH_2-, *-\overset{}{\underset{\underset{CH(CH_3)_2}{|}}{CH}}-CH_2-, *-\overset{}{\underset{\underset{CH(CH_3)_2}{|}}{CH}}-,$$

$$*-\overset{}{\underset{\underset{C_6H_5}{|}}{CH}}-, *-\overset{}{\underset{\underset{C_6H_5}{|}}{CH}}-CH_2-,$$

In the groups represented by formula (III), $A_1$, $A_2$, $A_3$ and $A_4$ each preferably represents —O—, —S—, —N($R_2$)CO—, —CON($R_2$)—, —N($R_2$)SO$_2$—, —SO$_2$N($R_2$)—, or —N($R_2$)CO$_2$—, and more preferably —O—, —N($R_2$)CO—, or —N($R_2$)SO$_2$—. $R_2$ and $R_3$ each preferably represents a hydrogen atom or an alkyl group, most preferably a hydrogen atom. $B_1$, $B_2$ and $B_3$ each preferably represents an alkylene group the principal chain of which has preferably from 1 to 3 carbon atoms and the total carbon atom number is from 1 to 20, a 1,2-phenylene group, a 1,3-phenylene group, or a 1,4-phenylene group, and $B_4$ preferably represents a substituted or unsubstituted alkyl group or a phenyl group. n is preferably 1.

In formula (IV), A preferably represents —CO— or —SO$_2$—, more preferably —CO—. $R_4$ represents a hydrogen atom or an alkyl group, and when $R_4$ represents an alkyl group, $R_4$ is preferably an unsubstituted alkyl group having from 1 to 4 carbon atoms, more preferably a hydrogen atom.

The compounds represented by formulae (I) and (II) are preferably diffusion resistant compounds, specifically, at least one group represented by $L_1$, $R_2$, $R_3$, $B_1$, $B_2$, $B_3$ and $B_4$ has 8 or more, preferably 12 or more, carbon atoms.

The combination of each substituent of the compounds represented by formulae (I) and (II) is such that preferably $R_1$ is an alkyl group, an alkoxy group or an aryloxy group, X is a halogen atom, an aryloxy group, a heterocyclic group, an alkylthio group or an arylthio group, $L_1$ is a divalent linking group, $A_1$, $A_2$, $A_3$ and $A_4$ in the group represented by formula (III) each is —O—, —S—, —N($R_2$)CO—, —CON($R_2$)—, —N($R_2$)SO$_2$—, —SO$_2$N($R_2$)—, or —N($R_2$)CO$_2$—, $R_2$ and $R_3$ each is a hydrogen atom or an alkyl group, $B_1$, $B_2$ and $B_3$ each is an alkylene group the principal chain of which has from 1 to 3 carbon atoms and the total carbon atom number is from 1 to 20, a 1,2-phenylene group, a 1,3-phenylene group, or a 1,4-phenylene group, $B_4$ is a substituted or unsubstituted alkyl group or a phenyl group, n is 1, A is —CO— or —SO$_2$—, and $R_4$ is a hydrogen atom or an unsubstituted alkyl group having from 1 to 4 carbon atoms; more preferably $R_1$ is an alkyl group, X is a chlorine atom or an aryloxy group, $L_1$ is a substituted or unsubstituted alkylene group the principal chain of which has from 1 to 3 carbon atoms, a substituted or unsubstituted 1,2-phenylene group, a substituted or unsubstituted 1,3-phenylene group or a substituted or unsubstituted 1,4-phenylene group, $A_1$, $A_2$, $A_3$ and $A_4$ in the group represented by formula (III) each is —O—, —N($R_2$)CO— or —N($R_2$)SO$_2$—, $R_2$ and $R_3$ each is a hydrogen atom, $B_1$, $B_2$ and $B_3$ each is an alkylene group the principal chain of which has from 1 to 3 carbon atoms and the total carbon atom number is from 1 to 20, a 1,2-phenylene group, a 1,3-phenylene group, or a 1,4-phenylene group, $B_4$ is a substituted or unsubstituted alkyl group or a phenyl group, n is 1, A is —CO— or —SO$_2$—, and $R_4$ is a hydrogen atom or an unsubstituted alkyl group having from 1 to 4 carbon atoms; and particularly preferably $R_1$ is a secondary or tertiary alkyl group, X is a chlorine atom or an aryloxy group, $L_1$ is a substituted or unsubstituted ethylene group, a substituted or unsubstituted 1,3-phenylene group or a substituted or unsubstituted 1,4-phenylene group, $A_1$, $A_2$, $A_3$ and $A_4$ in the group represented by formula (III) each is —O—, —N($R_2$)CO— or —N($R_2$)SO$_2$—, $R_2$ and $R_3$ each is a hydrogen atom, $B_1$, $B_2$ and $B_3$ each is an alkylene group the principal chain of which has from 1 to 3 carbon atoms and the total carbon atom number is from 1 to 20, a 1,2-phenylene group, a 1,3-phenylene group, or a 1,4-phenylene group, $B_4$ is a substituted or unsubstituted alkyl group or a phenyl group, n is 1, A is —CO—, and $R_4$ is a hydrogen atom.

Specific examples of the pyrazolotriazole magenta couplers represented by formulae (I) and (II) which can be used in the present invention are shown below, but the present invention is not limited thereto.

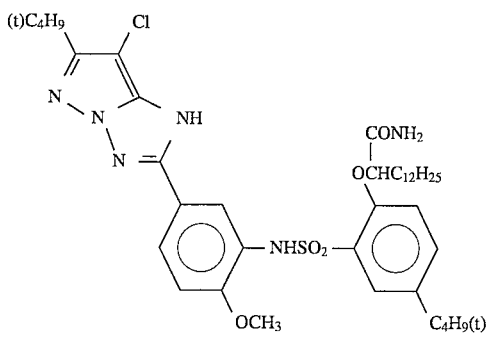

M-1

-continued
M-2
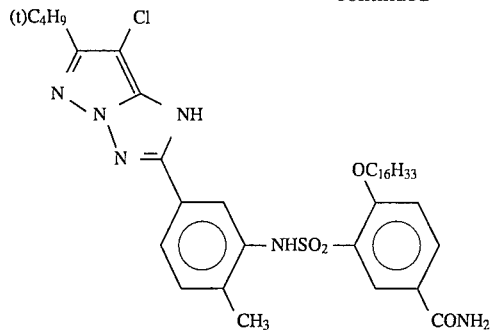
M-3
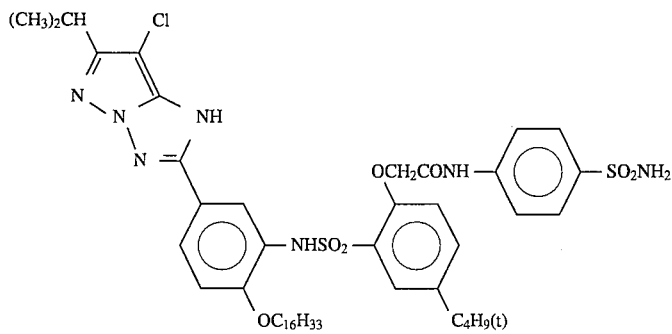
M-4
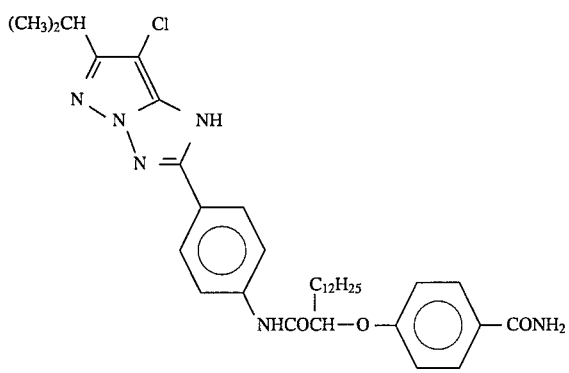
M-5
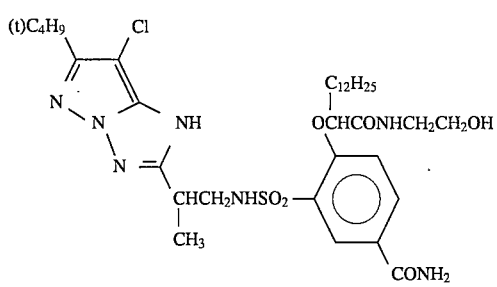
M-6
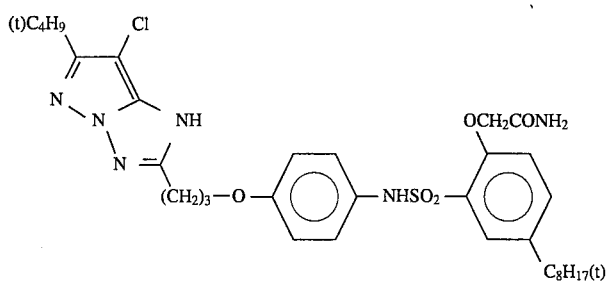

M-7
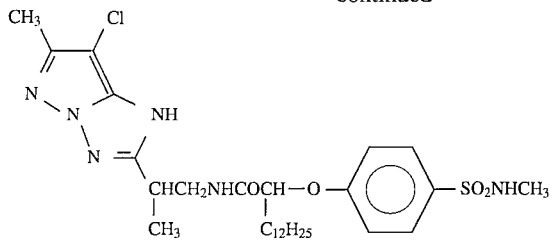
M-8
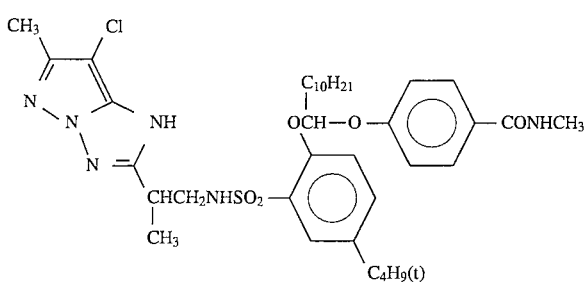
M-9
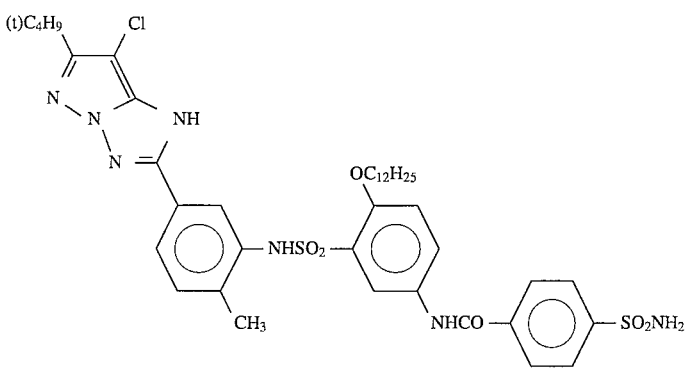
M-10
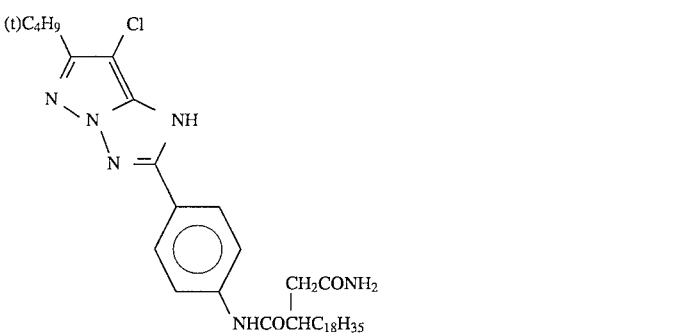
M-11
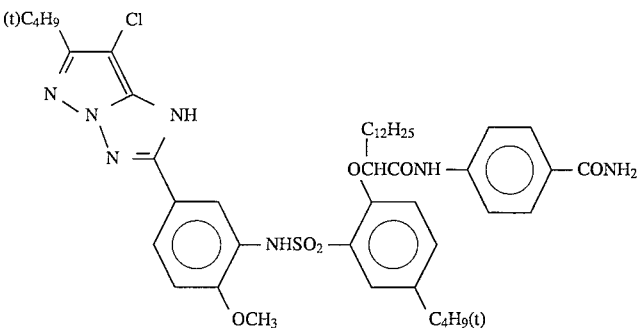

M-12
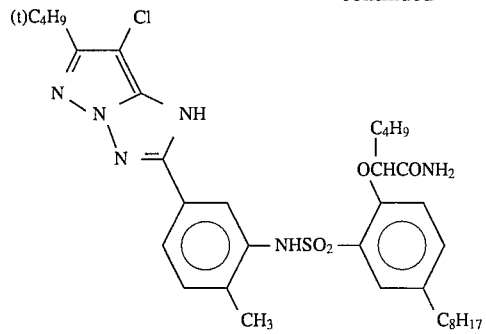
M-13
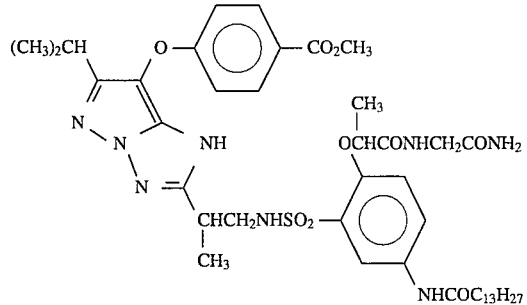
M-14
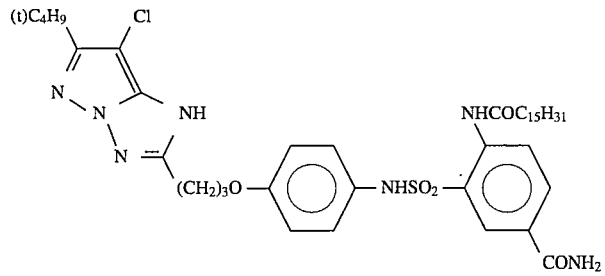
M-15
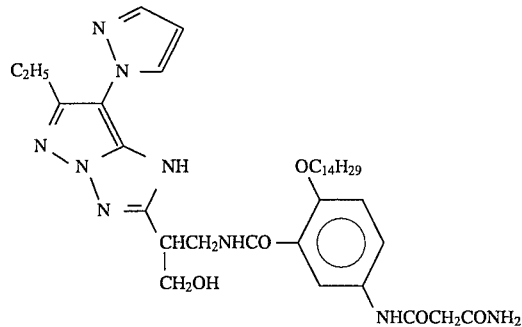
M-16
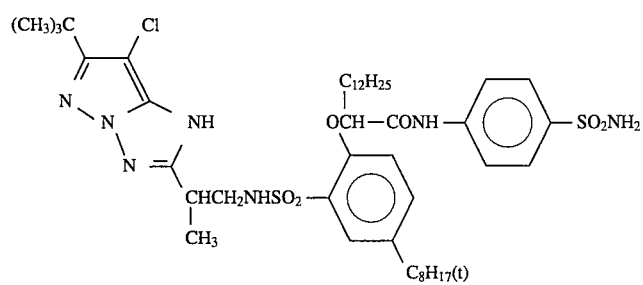

-continued
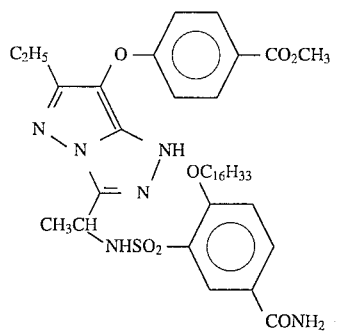
M-17
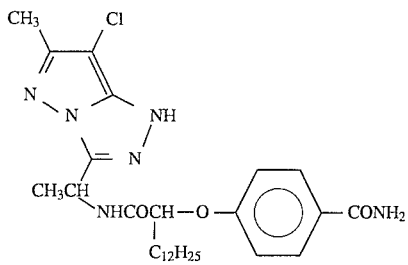
M-18
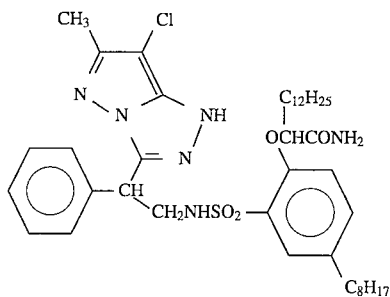
M-19
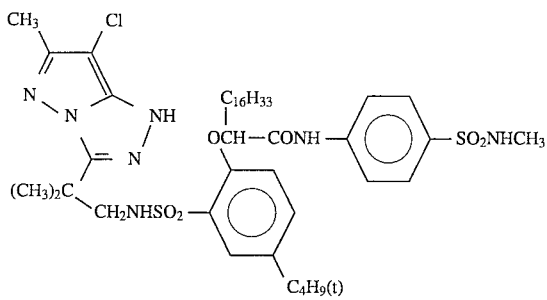
M-20
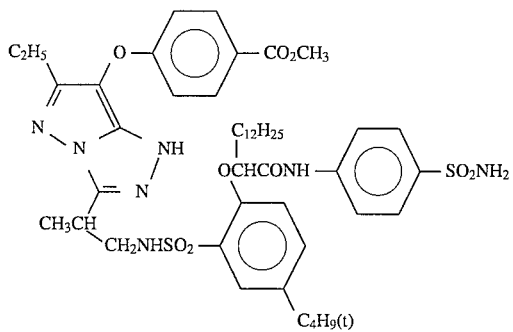
M-21

-continued
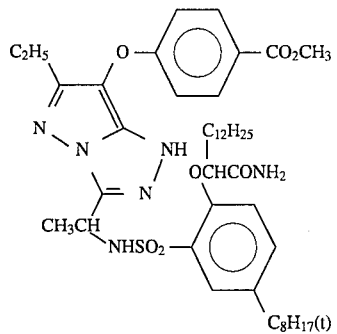
M-22
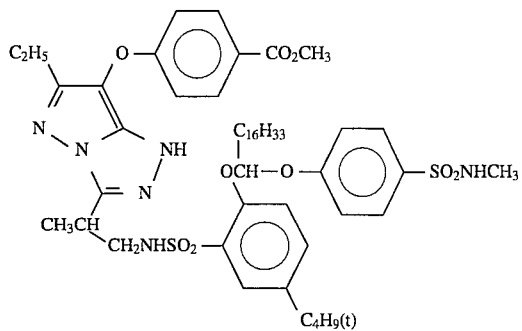
M-23
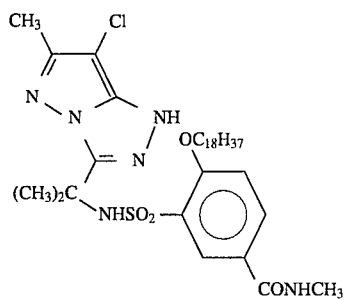
M-24
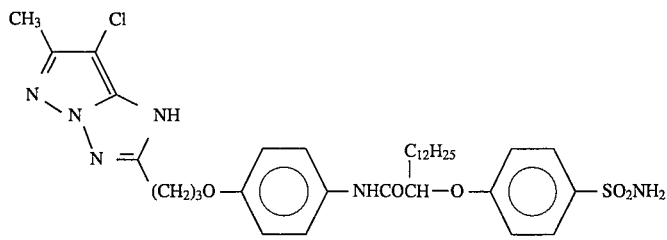
M-25
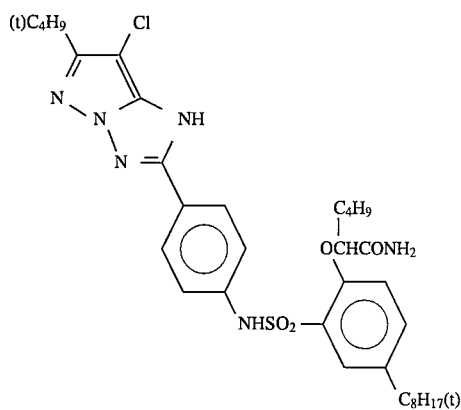
M-26

M-27

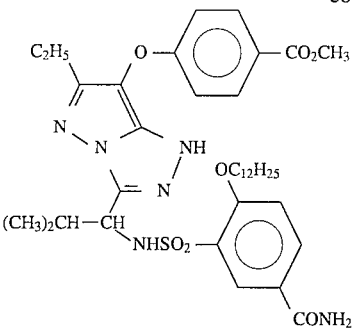

M-28

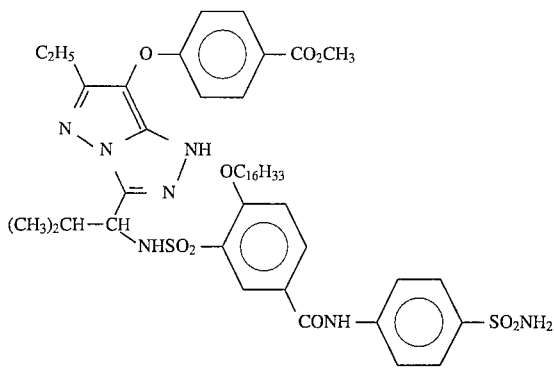

The pyrazolotriazole coupler represented by formula (I) or (II) for use in the present invention may be incorporated into any layer in the photographic material, preferably a green-sensitive layer, and when the green-sensitive layer is composed of plural green-sensitive layers having different sensitivities, it may be incorporated into any layer of the plural green-sensitive layer.

The couplers represented by formulae (I) and (II) of the present invention are added to a silver halide color photographic material in an amount of from $3 \times 10^{-5}$ to $3 \times 10^{-3}$ mol/m$^2$, preferably from $3 \times 10^{-4}$ to $2 \times 10^{-3}$ and more preferably from $1 \times 10^{-4}$ to $1.5 \times 10^{-3}$ mol/m$^2$.

The starting material of the pyrazolotriazole coupler represented by formula (I) of the present invention, a 5-amino-1H-pyrazole compound, can be synthesized according to the methods disclosed in JP-A-4-66573 and JP-A-4-66574. The starting material of the pyrazolotriazole coupler represented by formula (II) of the present invention, a 5-hydrazino-1H-pyrazole compound, can be obtained by diazotizing 5-aminopyrazoles (I-2) according to the method disclosed in JP-A-4-194846, and further reducing the above diazotized product. The skeleton of the pyrazolotriazole coupler of the present invention can be synthesized according to the methods disclosed in U.S. Pat. Nos. 3,725,067, 4,540,654, JP-B-4-79350, JP-B-4-79351 and JP-A-5-186470.

Specific synthesis examples of the compounds represented by formula (I) of the present invention are shown below.

SYNTHESIS EXAMPLE 1

Synthesis of Exemplified Compound M-16:
The exemplified Compound M-16 can be synthesized according to the following reaction scheme.

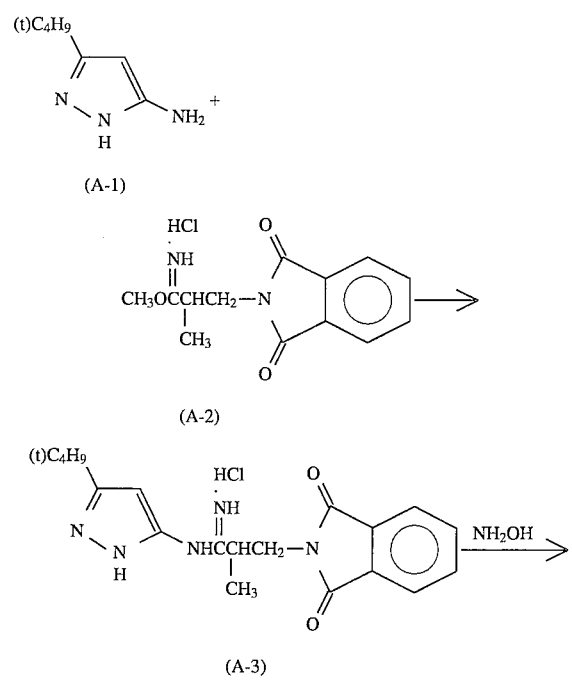

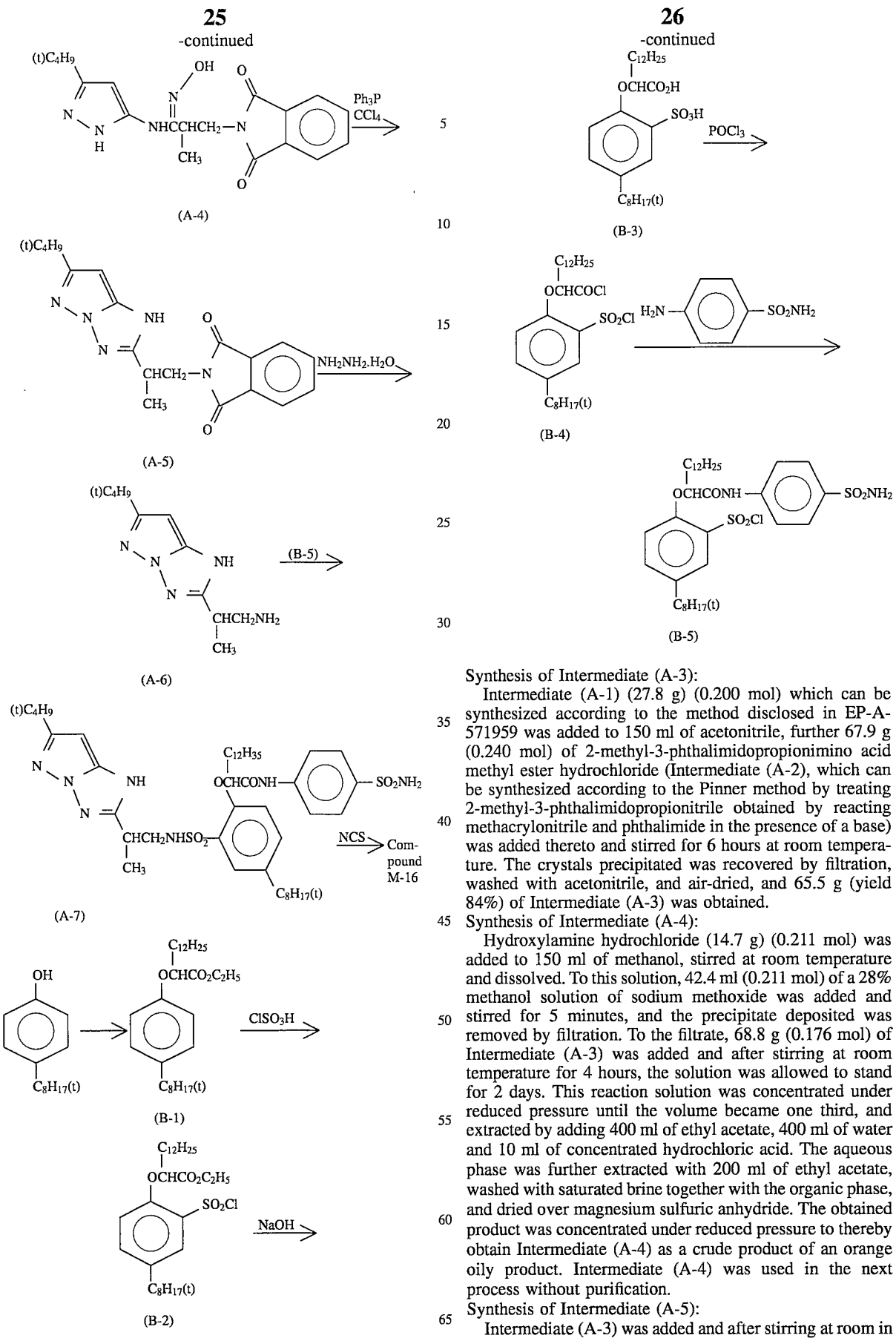

Synthesis of Intermediate (A-3):

Intermediate (A-1) (27.8 g) (0.200 mol) which can be synthesized according to the method disclosed in EP-A-571959 was added to 150 ml of acetonitrile, further 67.9 g (0.240 mol) of 2-methyl-3-phthalimidopropionimino acid methyl ester hydrochloride (Intermediate (A-2), which can be synthesized according to the Pinner method by treating 2-methyl-3-phthalimidopropionitrile obtained by reacting methacrylonitrile and phthalimide in the presence of a base) was added thereto and stirred for 6 hours at room temperature. The crystals precipitated was recovered by filtration, washed with acetonitrile, and air-dried, and 65.5 g (yield 84%) of Intermediate (A-3) was obtained.

Synthesis of Intermediate (A-4):

Hydroxylamine hydrochloride (14.7 g) (0.211 mol) was added to 150 ml of methanol, stirred at room temperature and dissolved. To this solution, 42.4 ml (0.211 mol) of a 28% methanol solution of sodium methoxide was added and stirred for 5 minutes, and the precipitate deposited was removed by filtration. To the filtrate, 68.8 g (0.176 mol) of Intermediate (A-3) was added and after stirring at room temperature for 4 hours, the solution was allowed to stand for 2 days. This reaction solution was concentrated under reduced pressure until the volume became one third, and extracted by adding 400 ml of ethyl acetate, 400 ml of water and 10 ml of concentrated hydrochloric acid. The aqueous phase was further extracted with 200 ml of ethyl acetate, washed with saturated brine together with the organic phase, and dried over magnesium sulfuric anhydride. The obtained product was concentrated under reduced pressure to thereby obtain Intermediate (A-4) as a crude product of an orange oily product. Intermediate (A-4) was used in the next process without purification.

Synthesis of Intermediate (A-5):

Intermediate (A-3) was added and after stirring at room in 450 ml of acetonitrile and stirred at room temperature. To the solution, 50.8 ml (0.512 mol) of carbon tetrachloride was added, 50.4 g (0.192 mol) of triphenylphosphine was further added and stirred at room temperature for 5 hours. The mixture was left to stand overnight, then the solvent was distilled off under reduced pressure, the residue was dissolved by adding a small quantity of acetonitrile, and extracted by adding 400 ml of ethyl acetate and 400 ml of water. After the organic phase was washed with 300 ml of saturated aqueous sodium bicarbonate then 300 ml of saturated brine, dried over magnesium sulfuric anhydride. The obtained product was concentrated under reduced pressure, then subjected to purification through a silica gel column chromatography (eluate: mixed solvent of chloroform/methanol) to obtain 37.2 g (yield: 82.7%) of Intermediate (A-5).

Synthesis of Intermediate (A-6):

Intermediate (A-5) (38.6 g) (0.110 mol) was dissolved in 150 ml of isopropyl alcohol, and heated under reflux while stirring. To the mixture, 5.87 ml (0.121 mol) of hydrazine hydrate was dropwise added over 20 minutes, and heated under reflux for further 3 hours. The reaction mixture was cooled in ice water, and insoluble matters precipitated were removed by filtration. The filtrate was concentrated under reduced pressure to obtain 24.8 g of a red oily product including Intermediate (A-6). The purity of the obtained product was estimated to be 56.7% by NMR spectrum.

Synthesis of Intermediate (B-2):

A mixture comprising 206 g (1.00 mol) of commercially available 4-t-octylphenol, 207 g (1.50 mol) of potassium carbonate and 500 ml of DMF was heated and stirred on a steam bath. To the above mixture, 335 g (1.00 mol) of 2-bromotetradecanoic acid ethyl ester was dropwise added over 40 minutes, and heated with stirring for 2 hours. Further, 67.2 g (0.200 mol) of 2-bromotetradecanoic acid ethyl ester was added to the mixture and heated with stirring for 2 hours. After cooling, the mixture was extracted with 1.5 liters of hexane and 2.0 liters of water, and the organic phase was washed with 1.0 liter of saturated aqueous sodium bicarbonate, then with 1.0 liter of saturated brine. The organic phase was dried over magnesium sulfuric anhydride, then concentrated under reduced pressure to obtain 529 g of a crude product of Intermediate (B-1) as a pale yellow oily product. This crude product (309 g) was dissolved in 1.2 liters of dichloromethane, cooled in a water bath, and stirred. To this reaction mixture, 56.0 ml (0.816 mol) of chlorosulfonic acid was dropwise added over 20 minutes, and stirred while cooling with water for 40 minutes then at room temperature for 40 minutes. To this reaction mixture, 250 ml of acetonitrile was added, then 500 ml of DMAC was gradually added, and stirred at 40° C. To the reaction mixture, 108 ml (1.17 mol) of phosphorus oxychloride was dropwise added over 20 minutes, and further stirred at 40° to 45° C. for 1 hour. Dichloromethane was distilled off under reduced pressure, the residue was poured into 2.0 liters of ice water, and the solution was extracted with 1.0 liter of hexane and 500 ml of ethyl acetate. The organic phase was washed with 1.5 liters of water, then with 1.5 liters of saturated brine, and dried over magnesium sulfuric anhydride. After concentration under reduced pressure, the residue was subjected to purification through a silica gel column chromatography (eluate: mixed solvent of hexane/ethyl acetate) to obtain 277 g (yield: 84.8%) of Intermediate (B-2) as a faint yellow oily product.

Synthesis of Intermediate (B-5):

Sodium hydroxide (20.0 g) (0.500 mol) was added to a mixed solution comprising 40 ml of water and 110 ml of ethanol and stirred at 50° C. Intermediate (B-2) (55.9 g) (0.100 mol) was dropwise added thereto over 20 minutes, and was heated under reflux for further 30 minutes. After cooling, the mixed solution was extracted by adding 52 ml of concentrated hydrochloric acid, 400 ml of ethyl acetate and 400 ml of water, and washed with 500 ml of 1N hydrochloric acid. After the organic phase was dried over magnesium sulfuric anhydride, concentrated under reduced pressure to thereby obtain 63.5 g of a crude product of Intermediate (B-3) as a faint yellow oily product. 46.0 g of the above obtained crude product was stirred together with 130 ml of acetonitrile and 65 ml of DMAC at room temperature. To the mixture, 26.7 ml (0.290 mol) of phosphorus oxychloride was dropwise added over 30 minutes, and stirred at room temperature for 30 minutes and further at 50° to 60° C. for 30 minutes. After cooling, the reaction mixture was extracted two times with 150 ml of hexane, and the hexane layer was concentrated under reduced pressure to thereby obtain 44.6 g of a crude product of Intermediate (B-4) as a pale yellow oily product. A mixture comprising 7.8 g (45.5 mmol) of sulfanilamide, 11.5 g (137 mmol) of sodium bicarbonate, 100 ml of water and 300 ml of ethyl acetate was cooled in a water bath and stirred. To this mixed solution, a solution obtained by diluting 25.0 g (45.5 mmol) of the above synthesized crude product of Intermediate (B-4) with 25 ml of ethyl acetate was dropwise added over 15 minutes, and stirred for further 30 minutes. The solution was separated and the organic phase was washed with 200 ml of saturated brine, then dried over magnesium sulfuric anhydride. After concentration under reduced pressure, the residue was subjected to purification through a silica gel column chromatography (eluate: mixed solvent of hexane/ethyl acetate) to obtain 19.4 g (yield: 62%) of Intermediate (B-5) as a faint yellow oily product.

Synthesis of Exemplified Compound M-16:

Intermediate (A-6) (8.80 g) (22.5 mmol) was dissolved in 35 ml of N,N-dimethylacetamide (DMAC), cooled in a water bath and stirred. To the solution, 3.46 ml (24.8 mmol) of triethylamine was added, then 16.1 g (23.6 mmol) of Intermediate (B-5) was added and stirred at room temperature for 20 minutes. The mixed solution was extracted by adding 120 ml of ethyl acetate, 150 ml of water and 2.5 ml of concentrated hydrochloric acid. The organic phase was washed with 100 ml of saturated brine. To the organic phase, 2.79 g (20.9 mmol) of N-chlorosuccinic acid imide was added, stirred and left to stand for 20 minutes. This ethyl acetate solution was extracted with 100 ml of water, washed with 100 ml of saturated brine, then dried over magnesium sulfuric anhydride. After concentration under reduced pressure, the residue was subjected to purification through a silica gel column chromatography (eluate: mixed solvent of hexane/ethyl acetate) to obtain 14.3 g (yield: 73%) of exemplified Compound M-16 as a colorless vitreous solid. The structure of the refined product was confirmed using $^1$H NMR spectrum and FAB mass spectrum.

SYNTHESIS EXAMPLE 2

Synthesis of Exemplified Compound M-22:

The exemplified Compound M-22 can be synthesized according to the following reaction scheme.

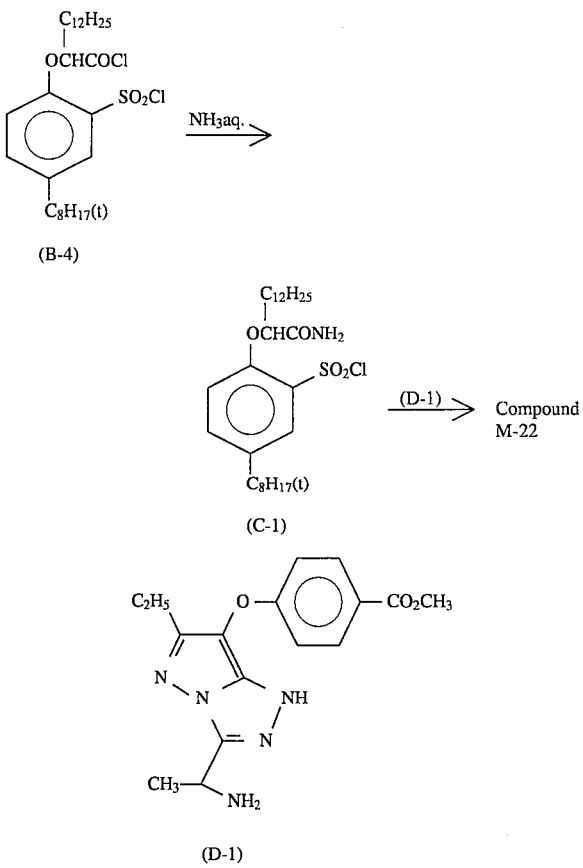

Synthesis of Intermediate (C-1):

A mixture comprising 1.57 ml (24.1 mmol) of a 29% aqueous ammonia, 6.05 g (72 mmol) of sodium bicarbonate, ml of water and 70 ml of ethyl acetate was cooled in a water bath and stirred. A solution obtained by diluting 13.2 g (24.0 mmol) of the crude product of Intermediate (B-4) synthesized in Synthesis Example 1 with 15 ml of ethyl acetate was dropwise added thereto over 15 minutes and stirred for further 30 minutes. The solution was separated and the organic phase was washed with 100 ml of saturated brine, then dried over magnesium sulfuric anhydride. After concentration under reduced pressure, the residue was subjected to purification through a silica gel column chromatography (eluate: mixed solvent of hexane/ethyl acetate) to obtain 10.8 g (yield: 78%) of Intermediate (C-1) as a faint yellow oily product.

Synthesis of Exemplified Compound M-22:

Intermediate (D-1) (4.22 g) (12.8 mmol) synthesized according to the method disclosed in Synthesis Example 1 of JP-A-5-204106 (the same compound as Compound (8) disclosed in Synthesis Example 1 of JP-A-5-204106) was dissolved in 20 ml of 2,6-lutidine and cooled in a water bath and stirred. A solution obtained by diluting 6.77 g (12.8 mmol) of Intermediate (C-1) with 10 ml of ethyl acetate was dropwise added thereto over 20 minutes and stirred for further 1 hour. The mixed solution was extracted by adding 100 ml of ethyl acetate, 100 ml of water and 15 ml of concentrated hydrochloric acid. The organic phase was washed with 80 ml of 1N hydrochloric acid then 100 ml of saturated brine. The organic phase was dried over magnesium sulfuric anhydride. After concentration under reduced pressure, the residue was subjected to purification through a silica gel column chromatography (eluate: mixed solvent of hexane/ethyl acetate) to obtain 3.66 g and 3.68 g (total: 7.34 g, yield: 70%) of two kinds of diastereomers of exemplified Compound M-22 as a pale brown vitreous solid.

$^1$H NMR spectrum (CDCl$_3$):

The compound eluted earlier with a silica gel column chromatography: δ(ppm) 9.66 (s, 1H), 7.90 (d, 2H), 7.77 (d, 1H), 7.44 (s, 1H), 7.42 (dd, 1H), 6.85 (d, 2H), 6.80 (d, 1H), 6.11 (d, 1H), 5.39 (brs, 1H), 5.04 (m, 1H), 4.72 (t, 1H), 3.86 (s, 3H), 2.56 (q, 2H), 2.00 (m, 2H), 1.74 (d, 3H), 1.66 (s, 2H), 1.55 (m, 2H), 1.4–1.2 (m, 24H), 1.18 (t, 3H), 0.87 (t, 3H), 0.65 (s, 9H) The compound eluted later with a silica gel column chromatography: δ(ppm) 10.12 (br, 1H), 7.9 (m, 3H), 7.66 (br, 1H), 7.50 (dd, 1H), 6.90 (m, 3H), 6.03 (d, 1H), 5.73 (brs, 1H), 5.05 (m, 1H), 4.81 (t, 1H), 3.86 (s, 3H), 2.59 (q, 2H), 2.06 (m, 2H), 1.70 (s, 2H), 1.58 (d, 3H), 1.5 (m, 2H), 1.4–1.2 (m, 24H), 1.09 (t, 3H), 0.86 (t, 3H), 0.67 (s, 9H)

Techniques and inorganic and organic materials which can be used in the present invention are disclosed in the following places of EP-A-436938 and the patents cited in the following places.

| | | |
|---|---|---|
| 1. | Layer Structure | line 34, page 146 to line 25, page 147 |
| 2. | Silver Halide Emulsion | line 26, page 147 to line 12, page 148 |
| 3. | Yellow Coupler | line 35, page 137 to line 33, page 146, lines 21 to 23, page 149 |
| 4. | Magenta Coupler | lines 24 to 28, page 149; line 5, page 3 to line 55, page 25 of EP-A-421453 |
| 5. | Cyan Coupler | lines 29 to 33, page 149; line 28, page 3 to line 2, page 40 of EP-A-432804 |
| 6. | Polymer Coupler | lines 34 to 38, page 149; line 39, page 113 to line 37, page 123 of EP-A-435334 |
| 7. | Colored Coupler | line 42, page 53 to line 34, page 137, lines 39 to 45, page 149 |
| 8. | Other Functional Coupler | line 1, page 7 to line 41, page 53, line 46, page 149 to line 3, page 150; line 1, page 3 to line 50, page 29 of EP-A-435334 |
| 9. | Preservative, Antibacterial Agent | lines 25 to 28, page 150 |
| 10. | Formalin Scavenger | lines 15 to 17, page 149 |
| 11. | Other Additives | lines 38 to 47, page 153; line 21, page 75 to line 56, page 84 of EP-A-421453, line 40, page 27 to line 40, page 37 |
| 12. | Dispersion Method | lines 4 to 24, page 150 |
| 13. | Support | line 32 to 34, page 150 |
| 14. | Film Thickness, Physical Properties of Film | lines 35 to 49, page 150 |
| 15. | Color Development Process | line 50, page 150 to line 47, page 151 |
| 16. | Desilvering Process | line 48, page 151 to line 53, page 152 |
| 17. | Automatic Processor | line 54, page 152 to line 2, page 153 |
| 18. | Washing and Stabilizing Processes | lines 3 to 37, page 153 |

EXAMPLE

The present invention will be illustrated in more detail with reference to the Example below, but it is not to be construed as limiting the invention.

Preparation of Sample No. 101:

A multilayer color photographic material was prepared as Sample No. 101 by coating each layer having the following composition on an undercoated cellulose triacetate film support having the thickness of 127 μm. The numeral corresponding to each component indicates the addition amount per m². The function of the additives is not limited to the use described.

First Layer: Antihalation Layer

| | |
|---|---|
| Black Colloidal Silver | 0.20 g |
| Gelatin | 1.90 g |
| Ultraviolet Absorbing Agent U-1 | 0.10 g |
| Ultraviolet Absorbing Agent U-3 | 0.040 g |
| Ultraviolet Absorbing Agent U-4 | 0.10 g |
| High Boiling Point Organic Solvent Oil-1 | 0.10 g |
| Microcrystal Solid Dispersion of Dye E-1 | 0.10 g |

Second Layer: Interlayer

| | |
|---|---|
| Gelatin | 0.40 g |
| Compound Cpd-C | 5.0 mg |
| Compound Cpd-J | 5.0 mg |
| Compound Cpd-K | 3.0 mg |
| High Boiling Point Organic Solvent Oil-3 | 0.10 g |
| Dye D-4 | 0.80 mg |

Third Layer: Interlayer

| | | |
|---|---|---|
| Surface and Interior Fogged Fine Grain Silver Iodobromide (average grain size: 0.06 μm, variation coefficient: 18%, AgI content: 1 mol %) | silver amount: | 0.050 g |
| Yellow Colloidal Silver | silver amount: | 0.030 g |
| Gelatin | | 0.40 g |

Fourth Layer: Low Sensitivity Red-Sensitive Emulsion

| | | |
|---|---|---|
| Emulsion A | silver amount: | 0.30 g |
| Emulsion B | silver amount: | 0.20 g |
| Gelatin | | 0.80 g |
| Coupler CC-1 | | 0.15 g |
| Coupler CC-2 | | 0.050 g |
| Coupler CC-3 | | 0.050 g |
| Coupler CC-4 | | 0.050 g |
| Compound Cpd-C | | 5.0 mg |
| Compound Cpd-J | | 5.0 mg |
| High Boiling Point Organic Solvent Oil-2 | | 0.10 g |
| Additive P-1 | | 0.10 g |

Fifth Layer: Middle Sensitivity Red-Sensitive Emulsion Layer

| | | |
|---|---|---|
| Emulsion B | silver amount: | 0.20 g |
| Emulsion C | silver amount: | 0.30 g |
| Gelatin | | 0.80 g |
| Coupler CC-1 | | 0.20 g |
| Coupler CC-2 | | 0.050 g |
| Coupler CC-3 | | 0.20 g |
| High Boiling Point Organic Solvent Oil-2 | | 0.10 g |
| Additive P-1 | | 0.10 g |

Sixth Layer: High Sensitivity Red-Sensitive Emulsion Layer

| | | |
|---|---|---|
| Emulsion D | silver amount: | 0.40 g |
| Gelatin | | 1.10 g |
| Coupler CC-1 | | 0.30 g |
| Coupler CC-2 | | 0.10 g |
| Coupler CC-3 | | 0.70 g |
| Additive P-1 | | 0.10 g |

Seventh Layer: Interlayer

| | |
|---|---|
| Gelatin | 0.60 g |
| Additive M-1 | 0.30 g |
| Color Mixing Preventive Cpd-1 | 2.6 mg |
| Dye D-5 | 0.020 g |
| Dye D-6 | 0.010 g |
| Compound Cpd-J | 5.0 mg |
| High Boiling Point Organic Solvent Oil-1 | 0.020 g |

Eighth Layer: Interlayer

| | | |
|---|---|---|
| Surface and Interior Fogged Silver Iodobromide (average grain size: 0.06 μm, variation coefficient: 16%, AgI content: 0.3 mol %) | silver amount: | 0.020 g |
| Yellow Colloidal Silver | silver amount: | 0.020 g |
| Gelatin | | 1.00 g |
| Additive P-1 | | 0.20 g |
| Color Mixing Preventive Cpd-A | | 0.10 g |
| Compound Cpd-C | | 0.10 g |

Ninth Layer: Low Sensitivity Green-Sensitive Emulsion Layer

| | | |
|---|---|---|
| Emulsion E | silver amount: | 0.10 g |
| Emulsion F | silver amount: | 0.20 g |
| Emulsion G | silver amount: | 0.20 g |
| Gelatin | | 0.50 g |
| Coupler MC-1 | | 0.25 g |
| Compound Cpd-B | | 0.030 g |
| Compound Cpd-D | | 0.020 g |
| Compound Cpd-E | | 0.020 g |
| Compound Cpd-F | | 0.040 g |
| Compound Cpd-J | | 10 mg |
| Compound Cpd-L | | 0.020 g |
| High Boiling Point Organic Solvent Oil-1 | | 0.02 g |
| High Boiling Point Organic Solvent Oil-2 | | 0.05 g |

Tenth Layer: Middle Sensitivity Green-Sensitive Emulsion

| | | |
|---|---|---|
| Emulsion G | silver amount: | 0.30 g |
| Emulsion H | silver amount: | 0.10 g |
| Gelatin | | 0.60 g |
| Coupler MC-1 | | 0.20 g |
| Compound Cpd-B | | 0.030 g |
| Compound Cpd-D | | 0.020 g |
| Compound Cpd-E | | 0.020 g |
| Compound Cpd-F | | 0.050 g |
| Compound Cpd-L | | 0.050 g |
| High Boiling Point Organic Solvent Oil-2 | | 0.05 g |

Eleventh Layer: High Sensitivity Green-Sensitive Emulsion

| | | |
|---|---|---|
| Emulsion I | silver amount: | 0.50 g |
| Gelatin | | 1.00 g |
| Coupler MC-1 | | 0.25 g |
| Compound Cpd-B | | 0.080 g |
| Compound Cpd-E | | 0.020 g |
| Compound Cpd-F | | 0.040 g |
| Compound Cpd-K | | 5.0 mg |
| Compound Cpd-L | | 0.020 g |
| High Boiling Point Organic | | 0.05 g |

-continued

| | | |
|---|---|---|
| Solvent Oil-1 | | |
| High Boiling Point Organic Solvent Oil-2 | | 0.020 g |

Twelfth Layer: Interlayer

| | |
|---|---|
| Gelatin | 0.60 g |
| Compound Cpd-L | 0.050 g |
| High Boiling Point Organic Solvent Oil-1 | 0.050 g |

Thirteenth Layer: Yellow Filter Layer

| | | |
|---|---|---|
| Yellow Colloidal Silver | silver amount: | 0.070 g |
| Gelatin | | 1.10 g |
| Color Mixing Preventive Cpd-A | | 0.010 g |
| Compound Cpd-L | | 0.010 g |
| High Boiling Point Organic Solvent Oil-1 | | 0.010 g |
| Microcrystal Solid Dispersion of Dye E-2 | | 0.050 g |

Fourteenth Layer: Interlayer

| | |
|---|---|
| Gelatin | 0.60 g |

Fifteenth Layer: Low Sensitivity Blue-Sensitive Emulsion

| | | |
|---|---|---|
| Emulsion J | silver amount: | 0.20 g |
| Emulsion K | silver amount: | 0.30 g |
| Gelatin | | 0.80 g |
| Coupler YC-1 | | 0.20 g |
| Coupler YC-2 | | 0.10 g |
| Coupler YC-3 | | 0.40 g |

Sixteenth Layer: Middle Sensitivity Blue-Sensitive Emulsion Layer

| | | |
|---|---|---|
| Emulsion L | silver amount: | 0.30 g |
| Emulsion M | silver amount: | 0.30 g |
| Gelatin | | 0.90 g |
| Coupler YC-1 | | 0.10 g |
| Coupler YC-2 | | 0.10 g |
| Coupler YC-3 | | 0.60 g |

Seventeenth Layer:

| | | |
|---|---|---|
| Emulsion N | silver amount: | 0.20 g |
| Emulsion O | silver amount: | 0.20 g |
| Gelatin | | 1.20 g |
| Coupler YC-1 | | 0.10 g |
| Coupler YC-2 | | 0.10 g |
| Coupler YC-3 | | 0.60 g |
| High Boiling Point Organic Solvent Oil-2 | | 0.10 g |

Eighteenth Layer: First Protective Layer

| | |
|---|---|
| Gelatin | 0.70 g |
| Ultraviolet Absorbing Agent U-1 | 0.20 g |
| Ultraviolet Absorbing Agent U-2 | 0.050 g |
| Ultraviolet Absorbing Agent U-5 | 0.30 g |
| Formalin Scavenger Cpd-H | 0.40 g |
| Dye D-1 | 0.15 g |
| Dye D-2 | 0.050 g |
| Dye D-3 | 0.10 g |

Nineteenth Layer: Second Protective Layer

| | | |
|---|---|---|
| Colloidal Silver | silver amount: | 0.10 mg |
| Fine Grain Silver Iodobromide Emulsion (average grain size: 0.06 μm, AgI content: 1 mol %) | silver amount: | 0.10 g |
| Gelatin | | 0.40 g |

Twentieth Layer: Third Protective Layer

| | |
|---|---|
| Gelatin | 0.40 g |
| Polymethyl Methacrylate (average particle size: 1.5 μm) | 0.10 g |
| Copolymer of Methyl Methacrylate/Acrylic Acid in Proportion of 4/6 (average particle size: 1.5 μm) | 0.10 g |
| Silicone Oil | 0.030 g |
| Surfactant W-1 | 3.0 mg |
| Surfactant W-2 | 0.030 g |

Further, Additives F-1 to F-8 were added to every emulsion layer in addition to the above components. Moreover, gelatin hardener H-1 and surfactants W-3, W-4, W-5 and W-6 for coating and emulsifying were added to every layer in addition to the above components.

In addition, phenol, 1,2-benzisothiazolin-3-one, 2-phenoxyethanol, phenethyl alcohol, p-benzoic acid butyl ester were added as antibacterial and antifungal agents.

The silver iodobromide emulsions used in Sample No. 101 are as shown in Table 1.

TABLE 1

| Emulsion Name | Characteristics of Grain | Sphere Corresponding Average Grain Size (μm) | Variation Coefficient (%) | AgI Content (%) |
|---|---|---|---|---|
| A | Monodisperse tetradecahedral grains | 0.28 | 16 | 4.0 |
| B | Monodisperse cubic internal latent image type grains | 0.30 | 10 | 4.0 |
| C | Monodisperse cubic grains | 0.38 | 10 | 5.0 |
| D | Monodisperse tabular grains, average aspect ratio: 3.0 | 0.68 | 8 | 2.0 |
| E | Monodisperse cubic grains | 0.20 | 17 | 4.0 |
| F | Monodisperse tetradecahedral grains | 0.25 | 16 | 4.0 |
| G | Monodisperse cubic internal latent image type grains | 0.40 | 11 | 4.0 |
| H | Monodisperse cubic grains | 0.50 | 9 | 3.5 |

TABLE 1-continued

| Emulsion Name | Characteristics of Grain | Sphere Corresponding Average Grain Size (μm) | Variation Coefficient (%) | AgI Content (%) |
|---|---|---|---|---|
| I | Monodisperse tabular grains, average aspect ratio: 5.0 | 0.80 | 10 | 2.0 |
| J | Monodisperse cubic grains | 0.30 | 18 | 4.0 |
| K | Monodisperse tetradecahedral grains | 0.45 | 17 | 4.0 |
| L | Monodisperse tabular grains, average aspect ratio: 5.0 | 0.55 | 10 | 2.0 |
| M | Monodisperse tabular grains, average aspect ratio: 8.0 | 0.70 | 13 | 2.0 |
| N | Monodisperse tabular grains, average aspect ratio: 6.0 | 1.00 | 10 | 1.5 |
| O | Monodisperse tabular grains, average aspect ratio: 9.0 | 1.20 | 15 | 1.5 |

TABLE 2

Spectral Sensitization of Emulsions A to I

| Emulsion Name | Sensitizing Dye Added | Addition Amount per mol of Silver Halide (g) |
|---|---|---|
| A | S-2 | 0.025 |
|   | S-3 | 0.25 |
|   | S-8 | 0.010 |
| B | S-1 | 0.010 |
|   | S-3 | 0.25 |
|   | S-8 | 0.010 |
| C | S-1 | 0.010 |
|   | S-2 | 0.010 |
|   | S-3 | 0.25 |
|   | S-8 | 0.010 |
| D | S-2 | 0.010 |
|   | S-3 | 0.10 |
|   | S-8 | 0.010 |
| E | S-4 | 0.50 |
|   | S-5 | 0.10 |
| F | S-4 | 0.30 |
|   | S-5 | 0.10 |
| G | S-4 | 0.25 |
|   | S-5 | 0.08 |
|   | S-9 | 0.05 |
| H | S-4 | 0.20 |
|   | S-5 | 0.060 |
|   | S-9 | 0.050 |
| I | S-4 | 0.30 |
|   | S-5 | 0.070 |
|   | S-9 | 0.10 |

TABLE 3

Spectral Sensitization of Emulsions J to O

| Emulsion Name | Sensitizing Dye Added | Addition Amount per mol of Silver Halide (g) |
|---|---|---|
| J | S-6 | 0.050 |
|   | S-7 | 0.20 |
| K | S-6 | 0.05 |
|   | S-7 | 0.20 |
| L | S-6 | 0.060 |
|   | S-7 | 0.22 |
| M | S-6 | 0.050 |
|   | S-7 | 0.17 |
| N | S-6 | 0.040 |
|   | S-7 | 0.15 |
| O | S-6 | 0.060 |
|   | S-7 | 0.22 |

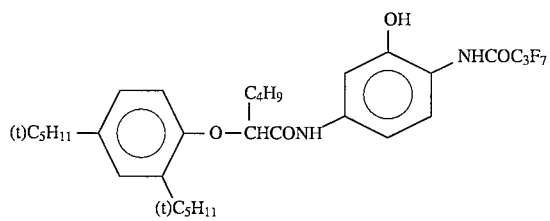

CC-1

-continued
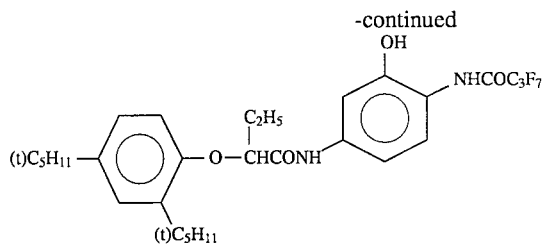
CC-2
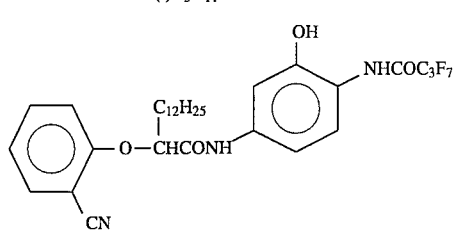
CC-3
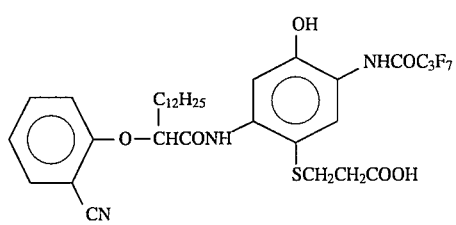
CC-4
(compound disclosed in JP-A-61-65248)  MC-1
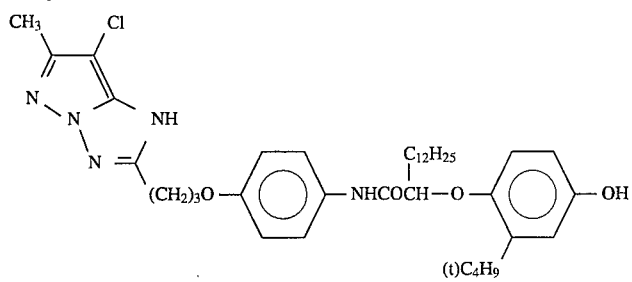
(compound disclosed in JP-B-4-3860)  MC-2
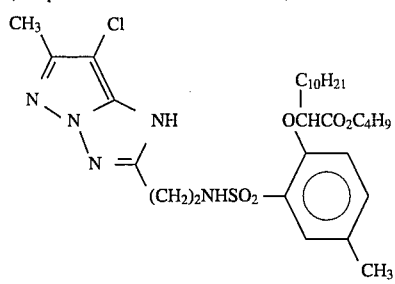
(compound disclosed in JP-B-5-39293)  MC-3
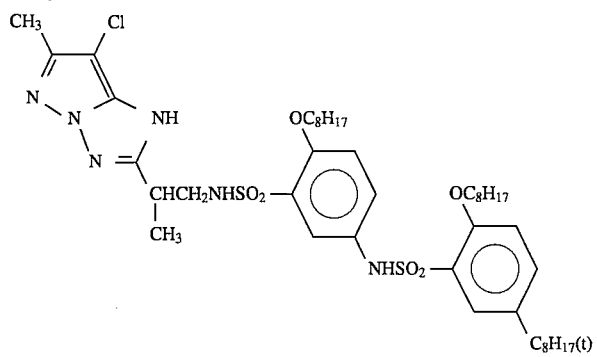

-continued
(compound disclosed in JP-A-6-222529) MC-4
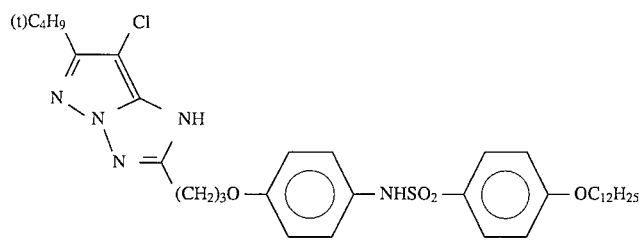
(compound disclosed in JP-A-6-222532) MC-5
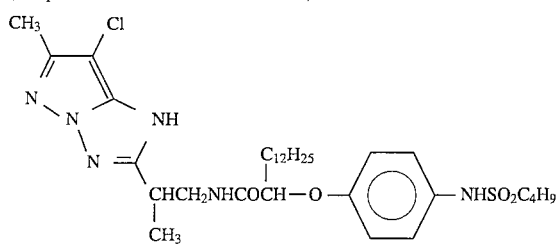
(compound disclosed in JP-A-6-43611) MC-6
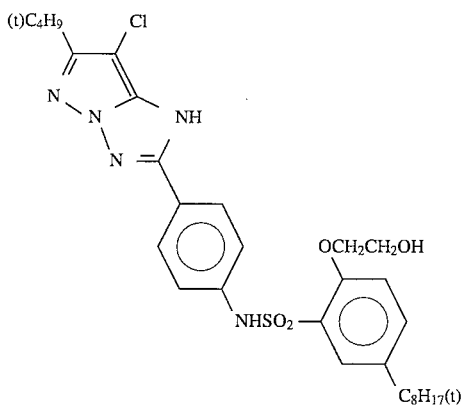
(compound disclosed in U.S. Pat. No. 4,443,536) MC-7
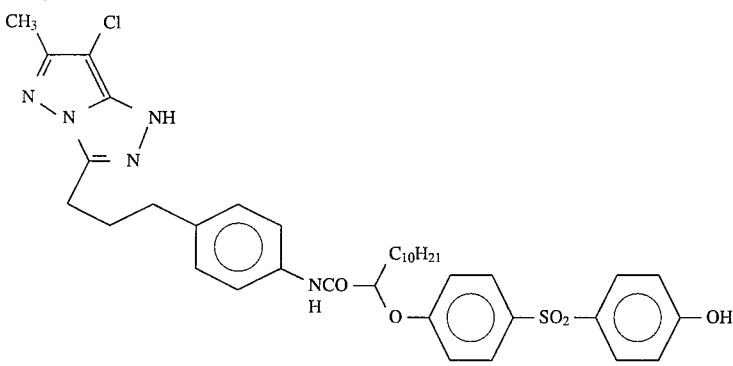
YC-1
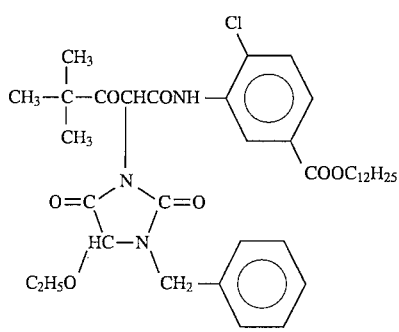

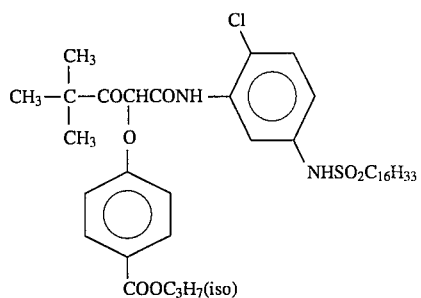
YC-2
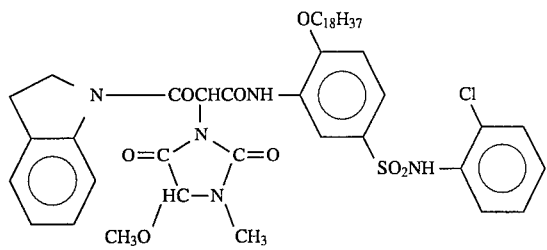
YC-3
Dibutyl Phthalate  Oil-1
Tricresyl Phosphate  Oil-2
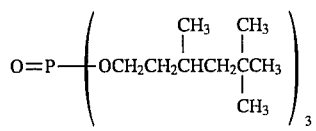
Oil-3
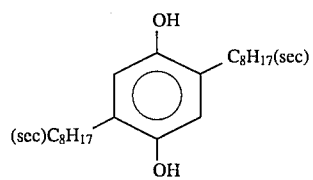
Cpd-A
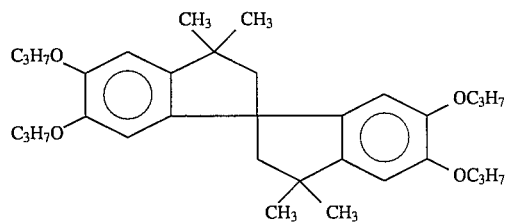
Cpd-B
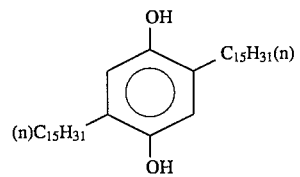
Cpd-C
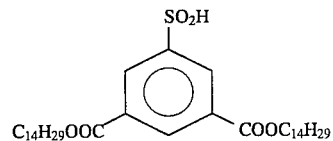
Cpd-D

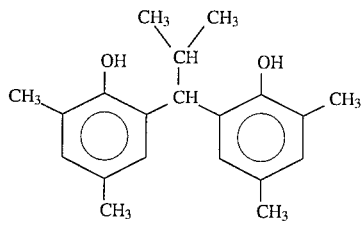
Cpd-E
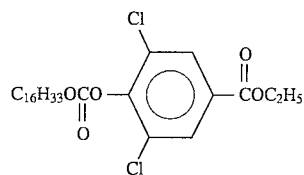
Cpd-F
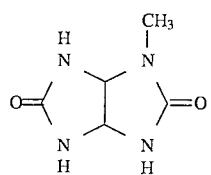
Cpd-H
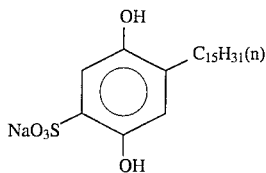
Cpd-I
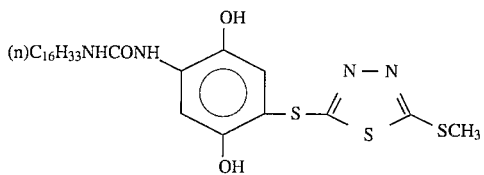
Cpd-J
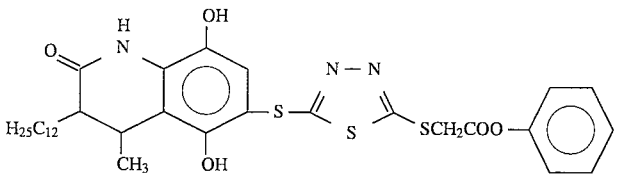
Cpd-K
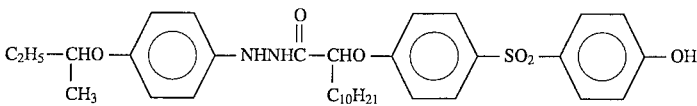
Cpd-L
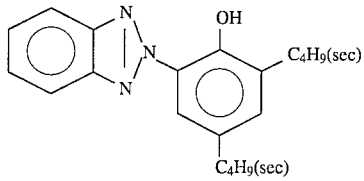
U-1
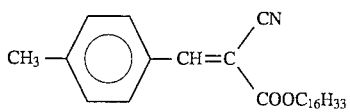
U-2

-continued
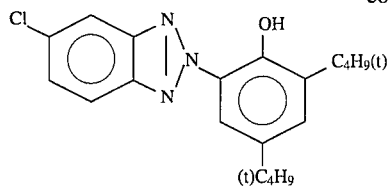
U-3
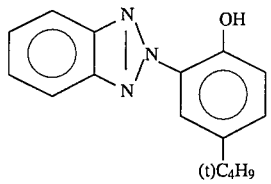
U-4
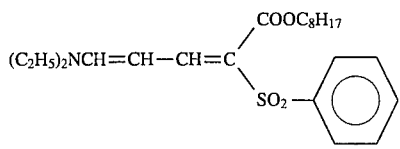
U-5
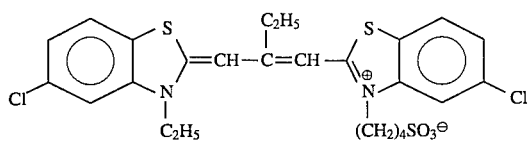
S-1
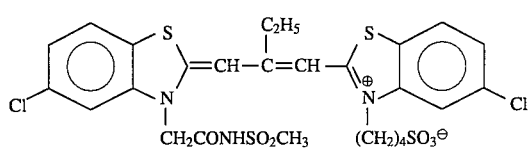
S-2
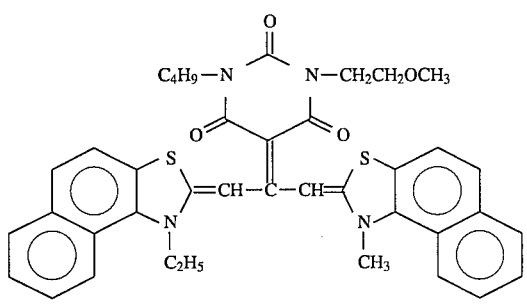
S-3
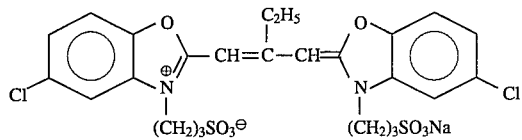
S-4
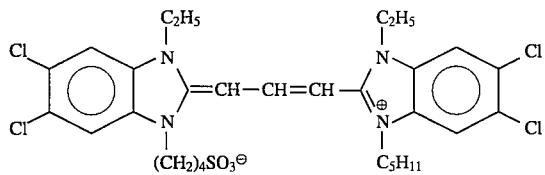
S-5
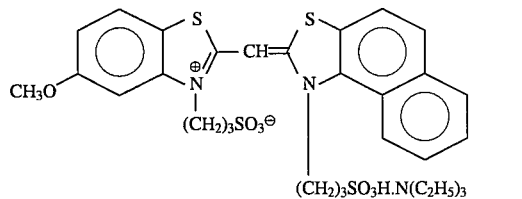
S-6

-continued
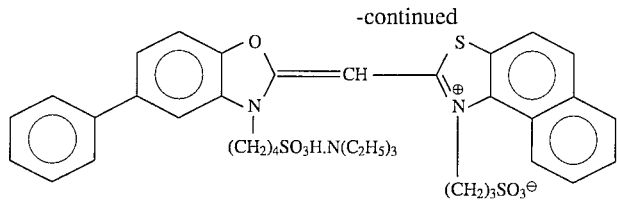 S-7
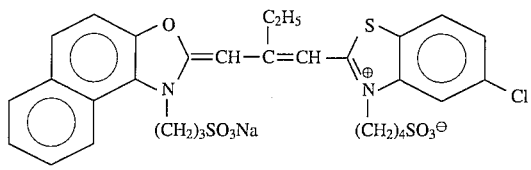 S-8
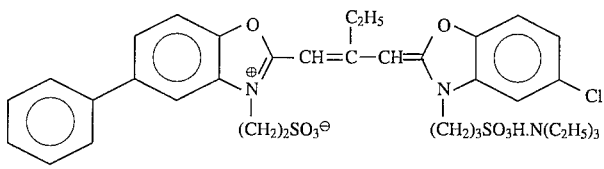 S-9
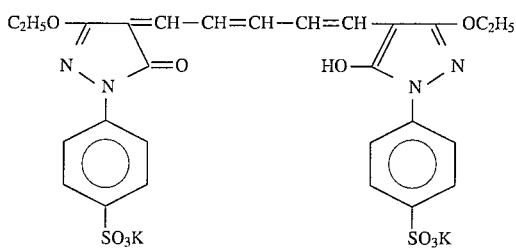 D-1
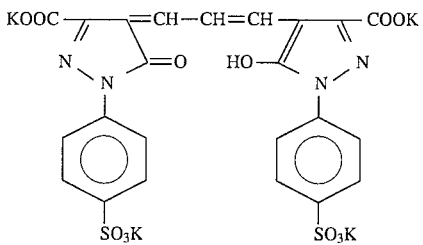 D-2
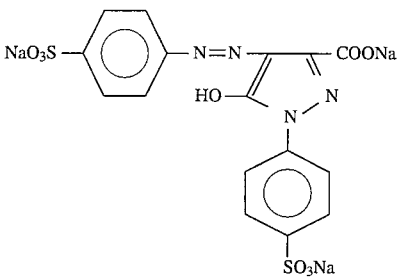 D-3
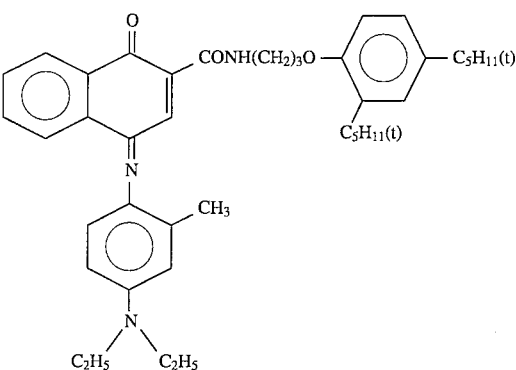 D-4

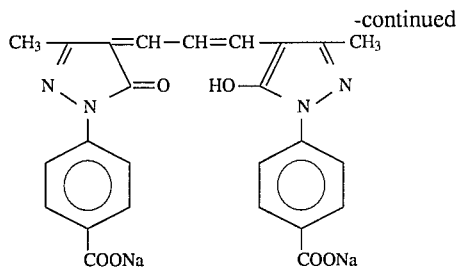
D-5
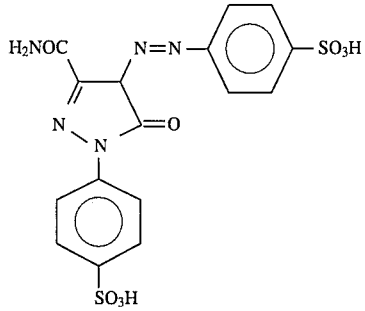
D-6
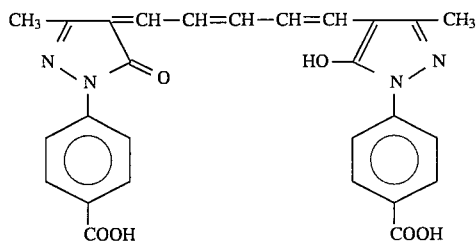
E-1
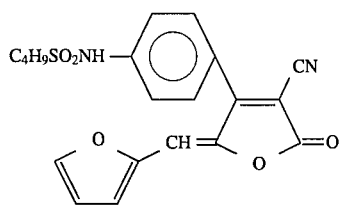
E-2
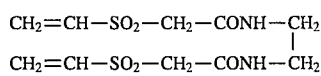
H-1
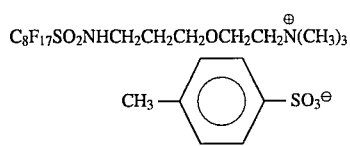
W-1
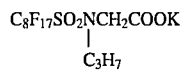
W-2
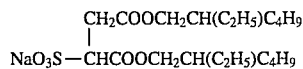
W-3
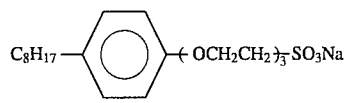
W-4
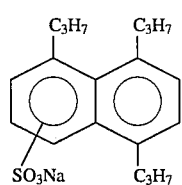
W-5

-continued
 W-6
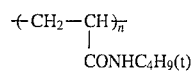 P-1
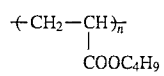 M-1
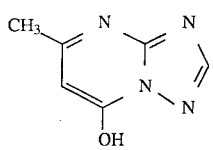 F-1
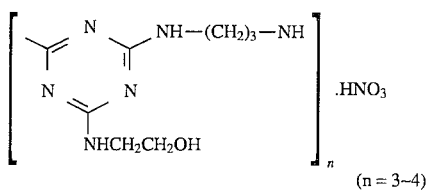 F-2
(n = 3~4)
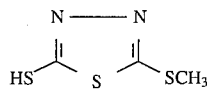 F-3
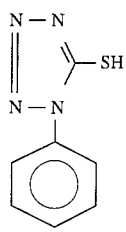 F-4
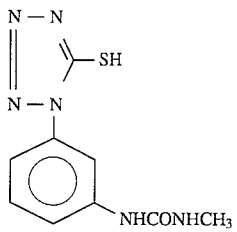 F-5
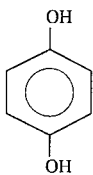 F-6
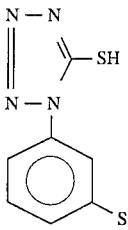 F-7
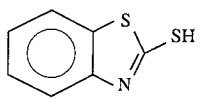 F-8

Sample Nos. 102 to 116 were prepared in the same manner as in Sample No. 101 except for changing the couplers in Ninth Layer, Tenth Layer and Eleventh Layer as shown in Table 4. The couplers were coated in equimolar amounts as MC-1 in Sample No. 101.

TABLE 4

| Sample No. | Couplers in 9th, 10th and 11th | Remarks |
| --- | --- | --- |
| 101 | MC-1 | Comparison |
| 102 | MC-2 | Comparison |
| 103 | MC-3 | Comparison |
| 104 | MC-4 | Comparison |
| 105 | MC-5 | Comparison |
| 106 | MC-6 | Comparison |
| 107 | MC-7 | Comparison |
| 108 | M-2 | Invention |
| 109 | M-4 | Invention |
| 110 | M-6 | Invention |
| 111 | M-7 | Invention |
| 112 | M-8 | Invention |
| 113 | M-17 | Invention |
| 114 | M-19 | Invention |
| 115 | M-25 | Invention |
| 116 | M-26 | Invention |

Sample Nos. 101 to 116 were wedge exposed with a white light of 4,800K, then subjected to the following development processing, and the magenta density at the maximum density part was measured. The results obtained are shown in Table 5. It is apparent from Table 5 that the couplers of the present invention have high color forming property.

TABLE 5

| Sample No. | Maximum Density (magenta) | Remarks |
| --- | --- | --- |
| 101 | 2.41 | Comparison |
| 102 | 2.50 | Comparison |
| 103 | 2.73 | Comparison |
| 104 | 2.18 | Comparison |
| 105 | 2.46 | Comparison |
| 106 | 2.15 | Comparison |
| 107 | 2.38 | Comparison |
| 108 | 3.21 | Invention |
| 109 | 3.10 | Invention |
| 110 | 3.04 | Invention |
| 111 | 3.35 | Invention |
| 112 | 3.28 | Invention |
| 113 | 3.31 | Invention |
| 114 | 3.36 | Invention |
| 115 | 3.01 | Invention |
| 116 | 3.25 | Invention |

Further, Sample Nos. 101 to 115 after development processing were irradiated with a xenon right (85,000 lux, 30° C., 60% RH) through a UV filter for one week, then the magenta density ($D_2$) was measured and compared with the magenta density before irradiation ($D_1$). The measuring point was the maximum density part of the sample before irradiation. The results obtained are shown in Table 6. It can be understood from Table 6 that the magenta dyes by the couplers of the present invention are excellent in light fastness. This is unexpected surprising effect.

TABLE 6

| Sample No. | Light Fastness $D_2/D_1$ (%) | Remarks |
| --- | --- | --- |
| 101 | 60 | Comparison |
| 102 | 63 | Comparison |
| 103 | 68 | Comparison |
| 104 | 72 | Comparison |
| 105 | 65 | Comparison |
| 106 | 71 | Comparison |
| 107 | 53 | Comparison |
| 108 | 89 | Invention |
| 109 | 84 | Invention |
| 110 | 88 | Invention |
| 111 | 78 | Invention |
| 112 | 76 | Invention |
| 113 | 78 | Invention |
| 114 | 77 | Invention |
| 115 | 74 | Invention |
| 116 | 85 | Invention |

| Processing Step | Processing Time (min) | Processing Temperature (°C.) | Tank Capacity (liter) | Replenishment Rate (ml/m$^2$) |
| --- | --- | --- | --- | --- |
| First Development | 6 | 38 | 12 | 2,200 |
| First Washing | 2 | 38 | 4 | 7,500 |
| Reversal | 2 | 38 | 4 | 1,100 |
| Color Development | 6 | 38 | 12 | 2,200 |
| Pre-bleaching | 2 | 38 | 4 | 1,100 |
| Bleaching | 6 | 38 | 12 | 220 |
| Fixing | 4 | 38 | 8 | 1,100 |
| Second Washing | 4 | 38 | 8 | 7,500 |
| Final Rinsing | 1 | 25 | 2 | 1,100 |

The composition of each processing solution used was as follows.

| | Tank Solution | Replenisher |
| --- | --- | --- |
| First Developing Solution | | |
| Pentasodium Nitrilo-N,N,N-trimethylenephosphonate | 1.5 g | 1.5 g |
| Pentasodium Diethylene-triaminepentaacetate | 2.0 g | 2.0 g |
| Sodium Sulfite | 30 g | 30 g |
| Potassium Hydroquinone-monosulfonate | 20 g | 20 g |
| Potassium Carbonate | 15 g | 20 g |
| Sodium Bicarbonate | 12 g | 15 g |
| 1-Phenyl-4-methyl-4-hydroxymethyl-3-pyrazolidone | 1.5 g | 2.0 g |
| Potassium Bromide | 2.5 g | 1.4 g |
| Potassium Thiocyanate | 1.2 g | 1.2 g |
| Potassium Iodide | 2.0 mg | — |
| Diethylene Glycol | 13 g | 15 g |
| Water to make | 1,000 ml | 1,000 ml |
| pH (adjusted with sulfuric acid or potassium hydroxide) | 9.60 | 9.60 |
| Reversal Solution | | |
| Pentasodium Nitrilo-N,N,N-trimethylenephosphonate | 3.0 g | same as the tank solution |
| Stannous Chloride Dehydrate | 1.0 g | |
| p-Aminophenol | 0.1 g | |
| Sodium Hydroxide | 8 g | |
| Glacial Acetic Acid | 15 ml | |
| Water to make | 1,000 ml | |
| pH (adjusted with acetic acid or sodium hydroxide) | 6.00 | |
| Color Developing Solution | | |
| Pentasodium Nitrilo-N,N,N-trimethylenephosphonate | 2.0 g | 2.0 g |
| Sodium Sulfite | 7.0 g | 7.0 g |
| Trisodium Phosphate 12 Hydrate | 36 g | 36 g |

| | Tank Solution | Replenisher |
|---|---|---|
| Potassium Bromide | 1.0 g | — |
| Potassium Iodide | 90 mg | — |
| Sodium Hydroxide | 3.0 g | 3.0 g |
| Citrazinic Acid | 1.5 g | 1.5 g |
| N-Ethyl-N-(β-methanesulfon-amidoethyl)-3-methyl-4-aminoaniline · ³⁄₂ Sulfate · Monohydrate | 11 g | 11 g |
| 3,6-Dithiaoctane-1,8-diol | 1.0 g | 1.0 g |
| Water to make | 1,000 ml | 1,000 ml |
| pH (adjusted with sulfuric acid or potassium hydroxide) | 11.80 | 12.00 |
| Prebleaching Solution | | |
| Disodium Ethylenediamine-tetraacetate Dehydrate | 8.0 g | 8.0 g |
| Sodium Sulfite | 6.0 g | 8.0 g |
| 1-Thioglycerol | 0.4 g | 0.4 g |
| Sodium Bisulfite Addition Products of Formaldehyde | 30 g | 35 g |
| Water to make | 1,000 ml | 1,000 ml |
| pH (adjusted with acetic or sodium hydroxide) | 6.30 | 6.10 |
| Bleaching Solution | | |
| Disodium Ethylenediamine-tetraacetate Dehydrate | 2.0 g | 4.0 g |
| Ammonium Ethylenediamine-tetraacetato Ferrate Dehydrate | 120 g | 240 g |
| Potassium Bromide | 100 g | 200 g |
| Ammonium Nitrate | 10 g | 20 g |
| Water to make | 1,000 ml | 1,000 ml |
| pH (adjusted with nitric acid or sodium hydroxide) | 5.70 | 5.50 |
| Fixing Solution | | |
| Ammonium Thiosulfate | 80 g | same as the tank solution |
| Sodium Sulfite | 5.0 g | same as the tank solution |
| Sodium Bisulfite | 5.0 g | same as the tank solution |
| Water to make | 1,000 ml | same as the tank solution |
| pH (adjusted with acetic acid or aqueous ammonia) | 6.60 | |
| Stabilizing Solution | | |
| 1,2-Benzisothiazolin-3-one | 0.02 g | 0.03 g |
| Polyoxyethylene-p-monononylphenyl Ether (average polymerization degree: 10) | 0.3 g | 0.3 g |
| Polymaleic Acid (average molecular weight: 2,000) | 0.1 g | 0.15 g |
| Water to make | 1,000 ml | 1,000 ml |
| pH | 7.0 | 7.0 |

According to the present invention, a silver halide color photographic material which provides images of good color forming property and high density as well as excellent in the storage stability of images can be obtained.

While the invention has been described in detail and with reference to specific examples thereof, it will be apparent to one skilled in the art that various changes and modifications can be made therein without departing from the spirit and scope thereof.

What is claimed is:

1. A silver halide color photographic material comprising a support having provided thereon at least one layer containing a pyrazolotriazole coupler represented by formula (I) or (II):

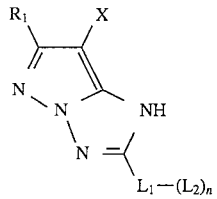

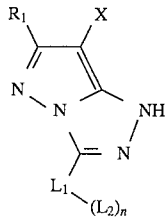

wherein $R_1$ represents a hydrogen atom, a halogen atom, or a substituent; X represents a hydrogen atom, a halogen atom, or a group capable of being splitted off by the reaction with an oxidation product of a developing agent; $L_1$ represents an (n+1)-valent linking group; $L_2$ represents a group represented by formula (III); and n represents 1 or 2, and when n is 2, two $L_2$'s may be the same or different;

$$-[(A_1)_a(B_1)_b(A_2)_c(B_2)_d(A_3)_e(B_3)_f(A_4)_g(B_4)_h] \quad (III)$$

wherein $A_1$, $A_2$, $A_3$ and $A_4$ each represents —O—, —S—, —NR$_2$—, —N(R$_2$)CO—, —CON(R$_2$)—, —N(R$_2$)SO$_2$—, —SO$_2$N(R$_2$)—, —CO$_2$—, —OCO—, —N(R$_2$)CON(R$_3$)—, —OCON(R$_2$)— or —N(R$_2$)CO$_2$—; $R_2$ and $R_3$ each represents a hydrogen atom, an alkyl group, an aryl group, an acyl group, an alkanesulfonyl group or an arenesulfonyl group; $B_1$, $B_2$ and $B_3$ each represents an alkylene group or an arylene group; $B_4$ represents an alkyl group or an aryl group; a, b, c, d, e, f and g each represents 0 or 1, h represents 1, provided that a-b=0, c-d=0 and e-f=0; and at least one group represented by $R_2$, $R_3$, $B_1$, $B_2$, $B_3$ and $B_4$ in the substituents represented by $L_2$ has a group represented by formula (IV):

$$-A-NH_2 \quad (IV)$$

wherein A represents —CO— or —SO$_2$—.

2. The silver halide color photographic material as claimed in claim 1, wherein $R_1$ is an alkyl group, an alkoxy group or an aryloxy group; X is a halogen atom, an aryloxy group, a heterocyclic group, an alkylthio group or an arylthio group; $L_1$ is a divalent linking group; $A_1$, $A_2$, $A_3$ and $A_4$ in the group represented by formula (III) each is —O—, —S—, —N(R$_2$)CO—, —CON(R$_2$)—, —N(R$_2$)SO$_2$—, —SO$_2$N(R$_2$)—, or —N(R$_2$)CO$_2$—; $R_2$ and $R_3$ each is a hydrogen atom or an alkyl group; $B_1$, $B_2$ and $B_3$ each is an alkylene group the principal chain of which has from 1 to 3 carbon atoms and the total carbon atom number is from 1 to 20, a 1,2-phenylene group, a 1,3-phenylene group, or a 1,4-phenylene group; $B_4$ is a substituted or unsubstituted alkyl group or a phenyl group; n is 1; and A is —CO— or —SO$_2$—.

3. The silver halide color photographic material as claimed in claim 2, wherein A is —CO.

4. The silver halide color photographic material as claimed in claim 1, wherein $R_1$ is an alkyl group; X is a chlorine atom or an aryloxy group; $L_1$ is a substituted or unsubstituted alkylene group the principal chain of which has from 1 to 3 carbon atoms, a substituted or unsubstituted 1,2-phenylene group, a substituted or unsubstituted 1,3-phenylene group or a substituted or unsubstituted 1,4-phenylene group; $A_1$, $A_2$, $A_3$ and $A_4$ in the group represented by formula (III) each is —O—, —N(R$_2$)CO— or —N(R$_2$)SO$_2$—, R$_2$ and R$_3$ each is a hydrogen atom; B$_1$, B$_2$ and B$_3$ each is an alkylene group the principal chain of which has from 1 to 3 carbon atoms and the total carbon atom number is from 1 to 20, a 1,2-phenylene group, a 1,3-phenylene group, or a 1,4-phenylene group; B$_4$ is a substituted or unsubstituted alkyl group or a phenyl group; n is 1; and A is —CO— or —SO$_2$—.

5. The silver halide color photographic material as claimed in claim 4, wherein A is —CO.

6. The silver halide color photographic material as claimed in claim 1, wherein R$_1$ is a secondary or tertiary alkyl group; X is a chlorine atom or an aryloxy group; L$_1$ is a substituted or unsubstituted ethylene group, a substituted or unsubstituted 1,3-phenylene group or a substituted or unsubstituted 1,4-phenylene group; A$_1$, A$_2$, A$_3$ and A$_4$ in the group represented by formula (III) each is —O—, —N(R$_2$)CO— or —N(R$_2$)SO$_2$—; R$_2$ and R$_3$ each is a hydrogen atom; B$_1$, B$_2$ and B$_3$ each is an alkylene group the principal chain of which has from 1 to 3 carbon atoms and the total carbon atom number is from 1 to 20, a 1,2-phenylene group, a 1,3-phenylene group, or a 1,4-phenylene group; B$_4$ is a substituted or unsubstituted alkyl group or a phenyl group; n is 1; and A is —CO—.

7. The silver halide color photographic material as claimed in claim 1, wherein R$_1$ is a halogen atom, an alkyl group, a cycloalkyl group, an alkenyl group, a heterocyclic group, a cyano group, a silyl group, a hydroxy group, a nitro group, an alkoxy group, a cycloalkyloxy group, an aryloxy group, a heterocyclic-oxy group, a silyloxy group, an acyloxy group, an alkoxycarbonyloxy group, a cycloalkyloxycarbonyloxy group, an aryloxycarbonyloxy group, a carbamoyloxy group, a sulfamoyloxy group, an alkanesufonyloxy group, an arenesulfonyloxy group, an acyl group, an alkoxycarbonyl group, an aryloxycarbonyl group, a carbamoyl group, an amino group, an anilino group, a heterocyclic amino group, a carbonamido group, a ureido group, an imido group, an alkoxycarbonylamino group, an aryloxycarbonylamino group, a sulfonamido group, a sulfamoylamino group, an azo group, an alkylthio group, an arylthio group, a heterocyclic-thio group, an alkylsulfinyl group, an arenesulfinyl group, an alkanesulfonyl group, an arenesulfonyl group, a sulfamoyl group, a sulfo group, or a phosphinoyl group; and X is a hydrogen atom, a halogen atom, an alkoxy group, an aryloxy group, an acyloxy group, a carbamoyloxy group, a sulfonyloxy group, a carbonamido group, a sulfonamido group, a carbamoylamino group, a heterocyclic group, an arylazo group, an alkylthio group, an arylthio group, or a heterocyclic-thio group.

8. The silver halide color photographic material as claimed in claim 7, wherein R$_1$ is an alkyl group, an aryl group, an alkoxy group, an aryloxy group, an alkylthio group, an arylthio group, a ureido group, an alkoxycarbonylamino group, an aryloxycarbonylamino group, or an amido group.

9. The silver halide color photographic material as claimed in claim 8, wherein R$_1$ is a tertiary alkyl group.

10. The silver halide color photographic material as claimed in claim 8, wherein X is chlorine or an aryloxy group.

* * * * *